(12) United States Patent
Kadowaki et al.

(10) Patent No.: US 7,230,145 B2
(45) Date of Patent: Jun. 12, 2007

(54) CATALYST FOR PRODUCING BOTH END-HYDROXYL GROUP-TERMINATED DIOLS, PROCESS FOR PRODUCING THE CATALYST, PROCESS FOR PRODUCING THE DIOLS BY USING THE CATALYST, AND BOTH END-HYDROXYL GROUP-TERMINATED DIOLS OBTAINED BY THE PROCESS

(75) Inventors: Yasushi Kadowaki, Oita (JP); Masato Kaneda, Oita (JP); Hiroshi Uchida, Oita (JP)

(73) Assignee: Showa Denko K.K., Tokyo (JP)

( * ) Notice: Subject to any disclaimer, the term of this patent is extended or adjusted under 35 U.S.C. 154(b) by 438 days.

(21) Appl. No.: 10/876,687

(22) Filed: Jun. 28, 2004

(65) Prior Publication Data

US 2004/0236156 A1 Nov. 25, 2004

Related U.S. Application Data

(62) Division of application No. 10/088,485, filed on Mar. 26, 2002, now abandoned.

(60) Provisional application No. 60/278,421, filed on Mar. 26, 2001.

(30) Foreign Application Priority Data

Mar. 22, 2001 (JP) ............................. 2001-081783
Dec. 7, 2001 (JP) ............................. 2001-373977

(51) Int. Cl.
*C07C 29/151* (2006.01)
*C07C 29/15* (2006.01)
*C07C 31/20* (2006.01)

(52) U.S. Cl. ...................... 568/865; 568/861; 568/866; 568/867

(58) Field of Classification Search ................ 568/861, 568/865, 866, 867
See application file for complete search history.

(56) References Cited

U.S. PATENT DOCUMENTS

| | | | |
|---|---|---|---|
| 2,895,819 | A | 7/1959 | Fiedler |
| 3,975,449 | A | 8/1976 | Suzuki |
| 4,590,313 | A | 5/1986 | Grey et al. |
| 5,744,419 | A | 4/1998 | Choudhary et al. |
| 5,777,166 | A | 7/1998 | Cordier et al. |
| 6,368,996 | B1 | 4/2002 | Mu et al. |

FOREIGN PATENT DOCUMENTS

| | | | |
|---|---|---|---|
| CN | 1141031 A | | 1/1997 |
| CN | 1272399 A | | 11/2000 |
| GB | 970 790 A | | 9/1964 |
| GB | 1581379 A | | 12/1980 |

*Primary Examiner*—Elvis O. Price
(74) *Attorney, Agent, or Firm*—Sughrue Mion, PLLC

(57) ABSTRACT

A process for producing a both end-hydroxyl group-terminated diol, wherein an epoxy alcohol represented by the general formula (1) is subjected to a hydrogenolysis reaction in the presence of a catalyst for producing both end-hydroxyl group terminated diols, which catalyst contains at least one element selected from the group consisting of Group V elements, Group VI elements, Group VII elements, Group VIII elements, Group IX elements, Group X elements, and Group XI elements in the periodic table, in the presence of at least one solvent selected from the group consisting of ethers, esters, aromatic hydrocarbon compounds, alicyclic hydrocarbon compounds and aliphatic hydrocarbon compounds, to thereby obtain a both end-hydroxyl group-terminated diol represented by general formula (2). General formula (1) and (2) are as described in the specification.

10 Claims, No Drawings

CATALYST FOR PRODUCING BOTH END-HYDROXYL GROUP-TERMINATED DIOLS, PROCESS FOR PRODUCING THE CATALYST, PROCESS FOR PRODUCING THE DIOLS BY USING THE CATALYST, AND BOTH END-HYDROXYL GROUP-TERMINATED DIOLS OBTAINED BY THE PROCESS

CROSS REFERENCE

This is a divisional of application Ser. No. 10/088,485 filed Mar. 26, 2002 now abandoned, which claims benefit of Provisional Application No. 60/278,421 filed Mar. 26, 2001; the disclosures of which are incorporated herein by reference.

TECHNICAL FIELD

The present invention relates to a catalyst for producing a diol terminated with a hydroxyl group at both ends thereof (hereinafter, referred to as "both end-hydroxyl group-terminated diol"), a process for producing such a catalyst, a process for producing both end-hydroxyl group-terminated diols by using the catalyst, and both end-hydroxyl group-terminated diols which have been obtained by such a production process.

More specifically, the present invention relates to a catalyst for producing both end-hydroxyl group-terminated diols, which is useful when both end-hydroxyl group-terminated diols are produced by the hydrogenolysis of an epoxy alcohol compound; a process for producing the catalyst; a process for producing both end-hydroxyl group-terminated diols by using the catalyst, and both end-hydroxyl group-terminated diols which have been obtained by the production process.

BACKGROUND ART

Both end-hydroxyl group-terminated diols are industrially useful as starting materials for resins such as polyester resins and polyurethane resins. Particularly, 1,3-propanediol is a compound having a great potential demand as a starting material for synthetic resins, particularly as a starting material for polyester fiber. Therefore, studies are being made to develop a process for producing this compound, at low cost, by a chemical production procedure, a biological production procedure, etc.

Heretofore, as the process for chemically producing the 1,3-propanediol, there are known various processes including: a production process for 1,3-propanediol wherein 3-hydroxypropionaldehyde (hereinafter simply referred to as "3-HPA") is synthesized by a hydration reaction of acrolein and the resultant product is then subjected to a hydrogenation reaction (Unexamined Japanese patent publication ("KOKAI"; hereinafter simply referred to as "JP-A") Hei. 10-212253); and a production process for 1,3-propanediol wherein 3-HPA is synthesized by a hydroformylation reaction of ethylene oxide and the resultant product is then subjected to a hydrogenation reaction (JP-A Hei. 11-515021); etc.

In any of these conventional processes, 1,3-propanediol is produced by finally hydrogenating 3-HPA, and therefore, these processes have a problem that unreacted 3-HPA is liable to remain in the resultant 1,3-propanediol product. In a case where polyester is synthesized by using 1,3-propanediol containing a carbonyl compound such as 3-HPA, it has been pointed out that such 1,3-propanediol is liable to cause odor or coloring in the polyester.

Accordingly, the 1,3-propanediol product should preferably contain no carbonyl compound such as 3-HPA, as completely as possible. However, it is difficult to remove these carbonyl compounds by a general purification method such as distillation, e.g., as disclosed in JP-A Hei. 6-40973 and JP-A Hei. 11-509828, etc.

Under these circumstances, in order to obtain 1,3-propanediol having a low content of carbonyl compounds such as 3-HPA, JP-A Hei. 6-40973 discloses a method of subjecting 3-HPA to a hydrogenation reaction through two stages, and JP-A Hei. 11-509828 discloses a method of removing carbonyl compounds which have been contained in 3-HPA by utilizing the reaction of the carbonyl compounds with an alkali. However, in any of these methods, it is difficult to obtain a 100% conversion for 3-HPA, and therefore it is necessary to remove the carbonyl compounds remaining in the resultant 3-HPA product. Such a removing operation increases the load on the production process for 1,3-propanediol, and this becomes a cause for increasing the production cost of 1,3-propanediol.

For solving the above-mentioned problems, there has been investigated a process for chemically producing 1,3-propanediol while no 3-HPA is used as the starting material. As one of these methods, there is a conceivable method wherein an epoxy alcohol compound (i.e., glycidol in this case) is subjected to hydrogenolysis.

As the reaction for obtaining a diol compound by the hydrogenolysis of an epoxy alcohol, for example, a hydrogenolysis reaction of glycidol by a Pd/C catalyst in methanol has been reported by Sajiki et al., in *Journal of Chemical Society, Chemical Communications*, pp. 1041-1042 (1999). However, according to this method, only 1,2-propanediol is produced and it is reported that the intended 1,3-propanediol cannot be obtained. In general, it is difficult to obtain such a hydroxyl group-terminated alcohol by the hydrogenolysis of a terminal epoxy group.

On the other hand, U.S. Pat. No. 3,975,449 discloses a process wherein a both end-hydroxyl group-terminated diol is produced by subjecting a hydroxyl, group-terminated epoxy alcohol having a di-substituted oxirane ring represented by the following formula (4) to hydrogenolysis in a solvent of water, alcohol or amide.

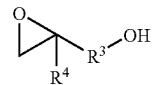

(wherein $R^3$ represents an alkylene group having 1 to 5 carbon atoms, and $R^4$ represents an alkyl group having 1 to 5 carbon atoms or a hydroxyalkyl group having 1 to 5 carbon atoms).

However, even in the method disclosed in this Patent publication, the selectivity factor corresponding to the conversion of the hydroxyl group-terminated epoxy alcohols having a mono-substituted oxirane ring represented by general formula (1) into both end-hydroxyl group-terminated diols is low, and Practical Example 6 of this Patent publication discloses that the selectivity factor corresponding to the conversion from glycidol into 1,3-propanediol is extremely low.

General Formula (1):

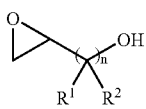

On the other hand, German Patent No. 1,139,477 discloses a process wherein a hydroxyl group-terminated alcohol is produced with a relatively good selectivity by the hydrogenolysis of 1,2-epoxyalkane which is a hydroxyl group-terminated epoxide having a mono-substituted oxirane ring. This patent publication has achieved an improvement in the selectivity for hydroxyl group-terminated alcohols in the hydrogenolysis of hydroxyl group-terminated 1,2-epoxyalkane having a mono-substituted oxirane ring, while such an improvement had been difficult until that time.

However, even by this method disclosed in this patent publication, the selectivity is not sufficiently high, unless the substituent of the oxirane ring has 7 or more carbon atoms, and it is found to be difficult to obtain hydroxyl group-terminated alcohols, similarly to the conventional methods.

As described above, there has never been known a process wherein an intended both end-hydroxyl group-terminated diol (such as 1,3-propanediol) is efficiently produced by the hydrogenolysis reaction of an epoxy alcohol compound (such as glycidol) with the number of carbon atoms in the substituent thereof being as small as 6 or less, among hydroxyl group-terminated epoxy compounds having a mono-substituted oxirane ring.

DISCLOSURE OF INVENTION

An object of the present invention is to provide a novel catalyst for producing both end-hydroxyl group-terminated diols, which is useful in efficiently producing both end-hydroxyl group-terminated diols by the hydrogenolysis reaction of an epoxy alcohol compound.

Another object of the present invention is to provide a process for producing the above-mentioned catalyst, a process for producing both end-hydroxyl group-terminated diols by using the catalyst, and both end-hydroxyl group-terminated diols which have been obtained by the above production process.

As a result of earnest study, the present inventors have found that, when a both end-hydroxyl group-terminated diol is intended to be produced by the hydrogenolysis reaction of an epoxy alcohol compound having a mono-substituted oxirane ring with the substituent having 6 or less carbon atoms, the both end-hydroxyl group-terminated diol can be produced with a high selectivity by conducting the hydrogenolysis reaction by use of a catalyst in the presence of a specific solvent. The present invention has been accomplished based on such a discovery.

More specifically, in a first aspect, the present invention relates to a catalyst for producing both end-hydroxyl group-terminated diols, which is usable in a process for producing a both end-hydroxyl group-terminated diol represented by general formula (2) by subjecting an epoxy alcohol compound represented by general formula (1) to a hydrogenolysis reaction in the presence of at least one solvent selected from the group consisting of ethers, esters, aromatic hydrocarbon compounds, alicyclic hydrocarbon compounds and aliphatic hydrocarbon compounds, the catalyst comprising at least one element selected from the group consisting of Group V, Group VI, Group VII, Group VIII, Group IX, Group X and Group XI of the periodic table.

General Formula (1);

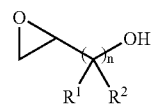

(1)

(wherein $R^1$ and $R^2$ each independently represents hydrogen, an alkyl group having 1 to 8 carbon atoms, a cycloalkyl group having 3 to 10 carbon atoms, or an aryl group having 6 to 13 carbon atoms and n represents an integer of 1 to 6);

General Formula (2):

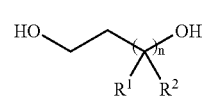

(2)

(wherein $R^1$ and $R^2$ each independently represents hydrogen, an alkyl group having 1 to 8 carbon atoms, a cycloalkyl group having 3 to 10 carbon atoms, or an aryl group having 6 to 13 carbon atoms and n represents an integer of 1 to 6).

In a second aspect, the present invention relates to a process for producing the catalyst for producing both end-hydroxyl group-terminated diols according to the first aspect of the present invention.

In a third aspect, the present invention relates to a process for producing both end-hydroxyl group-terminated diols by using the catalyst for producing both end-hydroxyl group-terminated diols according to the first aspect of the present invention.

Further, in a fourth aspect, the present invention relates to both end-hydroxyl group-terminated diols which have been produced by the process for producing both end-hydroxyl group-terminated diols of the third aspect of the present invention.

In addition, the present invention may include the following embodiments.

(1) A catalyst which contains at least one element selected from the group consisting of Group V elements, Group VI elements, Group VII elements, Group VIII elements, Group IX elements, Group X elements, and Group XI elements in the periodic table, and is to be used for subjecting an epoxy alcohol represented by the following general formula (1) to a hydrogenolysis reaction in the presence of at least one solvent selected from the group consisting of ethers, esters, aromatic hydrocarbon compounds, alicyclic hydrocarbon compounds and aliphatic hydrocarbon compounds, to thereby obtain a both end-hydroxyl group-terminated diol represented by the following general formula (2).

General Formula (1):

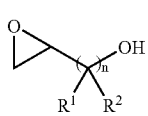

(wherein $R^1$ and $R^2$ each independently represents hydrogen, an alkyl group having 1 to 8 carbon atoms, a cycloalkyl group having 3 to 10 carbon atoms, or an aryl group having 6 to 13 carbon atoms and n represents an integer of 1 to 6);

General Formula (2):

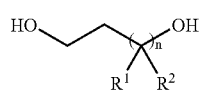

(wherein $R^1$ and $R^2$ each independently represents hydrogen, an alkyl group having 1 to 8 carbon atoms, a cycloalkyl group having 3 to 10 carton atoms, or an aryl group having 6 to 13 carbon atoms and n represents an integer of 1 to 6).

(2) A catalyst for producing both end-hydroxyl group-terminated diols as described in the above embodiment 1, which comprises at least one element selected from the group consisting of Fe, Co, Ni, Cu, Re and Ru.

(3) A catalyst for producing both end-hydroxyl group-terminated diols as described in the above embodiment (1) or (2), which is a sponge-type catalyst.

(4) A catalyst for producing both end-hydroxyl group-terminated diols as described in the above embodiment (1) or (2), which is a carrier-type catalyst.

(5) A catalyst for producing both end-hydroxyl group-terminated diols as described in the above embodiment 4, wherein the carrier comprises as least one species selected from the group consisting of: activated carbon, alumina, silica, silica alumina, zeolite, diatomaceous earth, titania, and zirconia.

(6) A process for producing a catalyst for producing both end-hydroxyl group-terminated diols as described in the above embodiment (3), which comprises at least the following Step (A) and step (B):

Step (A): a step of producing an alloy of aluminum and at least one element selected from the group consisting of Group V elements, Group VI elements, Group VII elements, Group VIII elements, Group IX elements, Group X elements, and Group XI elements in the periodic table;

Step (B): a step of eluting aluminum from the alloy obtained in Step (A), to thereby produce a catalyst for producing both end-hydroxyl group-terminated diols.

(7) A process for producing a catalyst for producing both end-hydroxyl group-terminated diols as described in the above embodiment (4) or (5), which comprises at least the following Step (C) and Step (D):

Step (C): a step of causing at least one element or a compound containing the at least one element to be carried on a carrier, the element being selected from the group consisting of Group v elements, Group VI elements, Group VII elements, Group VIII elements, Group IX elements, Group X elements, and Group XI elements in the periodic table, to thereby produce a carrier carrying thereon the at least one element;

Step (D): a step of hydrogenating the at least one element carried on the carrier obtained in Step (C), to thereby produce a catalyst for producing both end-hydroxyl group-terminated diols.

(8) A process for producing a both end-hydroxyl group-terminated diol, wherein an epoxy alcohol represented by the following general formula (1) is subjected to a hydrogenolysis reaction in the presence of a catalyst for producing both end-hydroxyl group-terminated diols according to any of the above embodiments (1) to (5), in the presence of at least one solvent selected from the group consisting of ethers, esters, aromatic hydrocarbon compounds, alicyclic hydrocarbon compounds and aliphatic hydrocarbon compounds, to thereby obtain a both end-hydroxyl group-terminated diol represented by the following general formula (2).

General Formula (1);

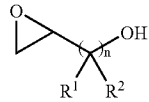

(wherein $R^1$ and $R^2$ each independently represents hydrogen, an alkyl group having 1 to 8 carbon atoms, a cycloalkyl group having 3 to 10 carbon atoms, or an aryl group having 6 to 13 carbon atoms and n represents an integer of 1 to 6);

General Formula (2):

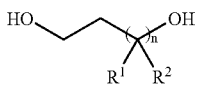

(wherein $R^1$ and $R^2$ each independently represents hydrogen, an alkyl group having 1 to 8 carbon atoms, a cycloalkyl group having 3 to 10 carbon atoms, or an aryl group having 6 to 13 carbon atoms and n represents an integer of 1 to 6).

(9) A process for producing a both end-hydroxyl group-terminated diol as described in the above embodiment (8), wherein the epoxy alcohol represented by the following general formula (1) is a compound which has been obtained by the epoxidizing an unsaturated alcohol compound represented by formula (3):

General Formula (3):

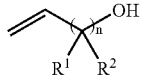

(wherein $R^1$ and $R^2$ each independently represents hydrogen, an alkyl group having 1 to 8 carbon atoms, a cycloalkyl group having 3 to 10 carbon atoms, or an aryl group having 6 to 13 carbon atoms and n represents an integer of 1 to 6).

(10) A process for producing a both end-hydroxyl group-terminated diol represented by the general formula (2), which comprises at least the following step (E) and Step (F):

Step (E): a step of epoxidizing an unsaturated alcohol compound represented by general formula (3), to thereby obtain an epoxy alcohol represented by the general formula (1);

Step (F): a step of subjecting the epoxy alcohol compound to a hydrogenolysis reaction in the presence of a catalyst for producing a both end-hydroxyl group-terminated diols according to any of claims 1-5, and in the presence of at least one solvent selected from the group consisting of ethers, esters, aromatic hydrocarbon compounds, alicyclic hydrocarbon compounds and aliphatic hydrocarbon compounds, to thereby obtain a both end-hydroxyl group-terminated diol represented by the following general formula (2).

General Formula (1):

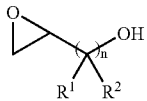

(1)

(wherein R¹ and R² each independently represents hydrogen, an alkyl group having 1 to 8 carbon atoms, a cycloalkyl group having 3 to 10 carbon atoms, or an aryl group having 6 to 13 carbon atoms and n represents an integer of 1 to 6);

General Formula (2):

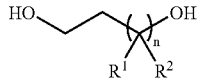

(2)

(wherein R¹ and R² each independently represents hydrogen, an alkyl group having 1 to 8 carbon atoms, a cycloalkyl group having 3 to 10 carbon atoms, or an aryl group having 6 to 13 carbon atoms and n represents an integer of 1 to 6)

General Formula (3):

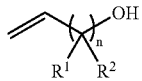

(wherein R¹ and R² each independently represents hydrogen, an alkyl group having 1 to 8 carbon atoms, a cycloalkyl group having 3 to 10 carbon atoms, or an aryl group having 6 to 13 carbon atoms and n represents an integer of 1 to 6);

(1). A process for producing a both end-hydroxyl group-terminated diol according to any of the above embodiments (8) to (10), wherein the epoxy alcohol represented by the following general formula (1) is at least one epoxy alcohol compound selected from the group consisting of; glycidol, 3,4-epoxy-1-butanol and 3,4-epoxy-2-butanol.

(12) A process for producing a both end-hydroxyl group-terminated diol as described in the above embodiments (9) or (10), wherein the an unsaturated alcohol compound represented by general formula (3) is at least one unsaturated alcohol compound selected from the group consisting of: allyl alcohol, 3-buten-1-ol and 3-buten-2-ol.

(13) A process for producing a both end-hydroxyl group-terminated diol according to any of claims 8-12, wherein the solvent is at least one species selected from the group consisting of diethyl ether, dibutyl ether, ethylene glycol dimethyl ether, ethylene glycol diethyl ether, 1,4-dioxane, benzene, toluene, xylene, cyclohexane, hexane, ethyl acetate, propyl acetate, isopropyl acetate and butyl acetate.

14. A both end-hydroxyl group-terminated diol, which has been produced by a process for producing a both end-hydroxyl group-terminated diol according to any of above embodiments (8) to (13)

BEST MODE FOR CARRYING OUT THE INVENTION

Hereinbelow, the present invention will be described in detail with reference to the accompanying drawings as desired. In the following description, "%" and "part(s)" representing a quantitative proportion or ratio are those based on mass, unless otherwise noted specifically.

(Catalyst for Producing Both End-Hydroxyl Group-Terminated Diols)

First, the first aspect of the present invention is described in detail.

In the first aspect, the present invention relates to a catalyst for producing both end-hydroxyl group-terminated diols, which is usable in a process for producing both end-hydroxyl group-terminated diols represented by general formula (2) by subjecting an epoxy alcohol compound represented by general formula (1) to a hydrogenolysis reaction in the presence of at least one solvent selected from the group consisting of ethers, esters, aromatic hydrocarbon compounds, alicyclic hydrocarbon compounds and aliphatic hydrocarbon compounds, the catalyst comprising at least one element selected from the group consisting of Group V, Group VI, Group VII, Group VIII, Group IX, Group X and Group XI of the periodic table;

General Formula (1):

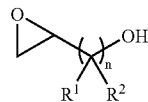

(1)

(wherein R¹ and R² each independently represents hydrogen, an alkyl group having 1 to 8 carbon atoms, a cycloalkyl group having 3 to 10 carbon atoms, or an aryl group having 6 to 13 carbon atoms and n represents an integer of 1 to 6);

General Formula (2):

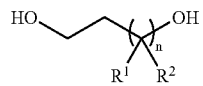

(2)

(wherein R¹ and R² each independently represents hydrogen, an alkyl group having 1 to 8 carbon atoms, a cycloalkyl group having 3 to 10 carbon atoms, or an aryl group having 6 to 13 carbon atoms and n represents an integer of 1 to 6).

The catalyst for producing both end-hydroxyl group-terminated diols according to the first aspect of the present invention comprises at least one element selected from the group consisting of Group V, Group VI, Group VII, Group VIII, Group IX, Group X and Group XI of the periodic table. In the present invention, the "periodic table" refers to that according to Nomenclature of Inorganic Chemistry, Revised Edition, 1989, International Union of Pure and Applied Chemistry.

The catalyst may preferably comprise at least one element selected from the group consisting of Cr, Mn, Fe, Co, Ni, Cu, Mo, W, Re and Ru. The catalyst may more preferably comprise at least one element selected from the group consisting of Fe, Co, Ni, Cu, Re and Ru.

According to the present inventors' investigation, it is presumed that the reason why such elements are effective as a catalyst for producing both end-hydroxyl group-terminated diols is that such an element has a high affinity for the oxygen atom of the epoxy group of a reactant (or substrate) compound, and therefore this affinity facilitates the cleavage wherein the bonding between the oxygen atom and secondary or tertiary carbon is cleaved via a radical or a carbonium ion.

The catalyst for producing both end-hydroxyl group-terminated diols according to the first aspect of the present invention may contain any element other than the above-described elements or any compound, as long as it does not substantially inhibit the intended reaction. In view of the catalyst activity, the above-mentioned at least one element selected from the group consisting of Group V, Group VI, Group VII, Group VIII, Group IX, Group X and Group XI of the periodic table may preferably be contained in the catalyst in an amount of 1% or more, more preferably 2% or more, particularly preferably 5% or more (based on the total mass of the catalyst including the at least one element per se).

The form or shape of the catalyst for producing both end-hydroxyl group-terminated diols according to the first aspect of the present invention is not particularly limited and may be either of the homogeneous-type catalyst or heterogeneous-type catalyst. In view of the ease in the operation of separating the catalyst from the reaction mixture after the reaction, the heterogeneous catalyst is preferred. However, the homogeneous catalyst is also usable in the present invention.

(Homogeneous Catalyst)

The homogeneous catalyst may have any form or shape, as long as the catalyst can be dissolved in a reaction mixture at the time of the reaction. More specifically, for example, the catalyst may have a salt form of the element, such as chloride, bromide, iodide, nitrate, sulfate, carboxylate or carbonate, or a so-called complex form where a ligand is bonded to the element.

(Ligand)

In the present invention, the ligand which is usable in the formation of a complex is not particularly limited, and the ligand may be at least one species selected from known ligands. Specific examples thereof may include: carbonyl ligands; phosphorus-containing ligands such as triphenylphosphine, trimethylphosphine, triphenyl phosphite and triphenylphosphine oxide; nitrogen-containing ligands such as ammonia, ethylenediamine and pyridine; ether ligands such as diethyl ether, ethylene glycol dimethyl ether, tetrahydrofuran and 1,4-dioxane; olefin ligands such as ethylene, 1,4-cyclooctadiene and cyclopentadienyl anion; diketonate ligands such as acetylacetonate anion; cyano ligands; halogen ligands such as chloro, bromo and iodo; alkoxide ligands such as methoxide, ethoxide, butoxide and phenoxide; hydride ligands; and ligands comprising a combination of at least two species of the above-mentioned ligands. Of course, the ligands usable in the present invention are not limited to these specific ligands.

(Use of Homogeneous Catalyst)

The homogeneous catalyst may be used in an embodiment wherein the catalyst is preliminarily dissolved in a solvent and then the resultant mixture is used for the reaction, or the catalyst may be used in an embodiment wherein it is preliminarily dissolved in the reactant epoxy alcohol and then the resultant mixture is used for the reaction. Alternatively, it is also possible that the catalyst is simultaneously charged to a reaction system together with a solvent and starting material, and then the resultant mixture is subjected to the reaction. Further, it is also possible that the catalyst dissolved in a solvent is preliminarily brought into contact with hydrogen so as to be activated, and then the activated catalyst is subjected to the reaction with an epoxy alcohol.

(Heterogeneous Catalyst)

In the case of the heterogeneous catalyst for producing both end-hydroxyl group-terminated diols according to the first aspect of the present invention, the form or shape of the element or compound usable in the catalyst is not particularly limited. The heterogeneous catalyst may preferably be used in any form of a metal type, a sponge type, an oxide, a hydroxide, a boride, a phosphide, etc.

With respect to the element to be contained in the catalyst according to the first aspect of the present invention, an element in the above-described form or a compound containing the element may be used as it is in the intended reaction, or such an element or compound may be used in the reaction as a so-called carrier-type catalyst which has been obtained by causing the element or compound to be carried on an appropriate carrier (or support).

(Sponge-Type Catalyst)

In a case where the element is used as it is as the catalyst for producing both end-hydroxyl group-terminated diols according to the first aspect of the present invention, one preferred example of the catalyst is a sponge-type catalyst. The term "sponge-type catalyst" as used herein means a porous metal-containing catalyst. "Sponge Ni" which is one example of the sponge-type catalyst is described, for example, in *Tetrahedron Lett.*, Vol. 32, No. 40, pp. 5885-5888 (1999).

Further, as the element or compound containing the element, which is usable as it is as the catalyst, examples thereof may include: sponge catalysts such as sponge Fe, sponge-Co, sponge-Ni, sponge-Cu and sponge-Ru; oxide catalysts such as V oxide, Cr oxide, Fe oxide, Co oxide, Ni oxide, Cu oxide, Mo oxide, W oxide, Re oxide, Ru oxide, Rh oxide, Pd oxide, Pt oxide, Cr oxide-Fe oxide, Cr oxide-Cu oxide, Cr oxide-Ni oxide, Cr oxide-Zn oxide and Cr oxide-Cu oxide-Zn oxide; hydroxide catalysts such as Cr hydroxide, Mn hydroxide, Fe hydroxide, Co hydroxide, Ni hydroxide, Cu hydroxide, Ru hydroxide, Rh hydroxide, Pd hydroxide and Pt hydroxide; boride catalysts such as Co boride and Ni boride; and phosphide catalysts such as Ni phosphide. These catalysts may be used individually or in combination of two or more species thereof.

(Carrier-Type Catalyst)

In a case where the catalyst for producing both end-hydroxyl group-terminated diols according to the first aspect of the present invention is a carrier-type catalyst, the carrier usable in such an embodiment is not particularly limited and may appropriately be selected from known carriers. Specific examples thereof may include: activated carbon (hereinafter sometimes simply referred to as "carbon"), silica, alumina, silica alumina, zeolite, titania, zirconia, magnesia, diatomaceous earth (or kieselguhr), barium sulfate, barium carbonate, calcium carbonate and magnesium carbonate. Among these, it is preferred to use activated carbon, silica, alumina, silica alumina, zeolite, titania, zirconia and diatomaceous earth, in view of the effect thereof on reaction, the surface area at the preparation of the catalyst or the industrial practicability such as strength of carrier.

In a case where an element or a compound containing the element, which is the active species of the catalyst, is caused to be carried on a carrier, the amount of the element or compound containing the element and the carrier are preferably such that the amount of the element or compound containing the element is from 0.01 to 150 mass % (or % by mass) based on the total mass of the carrier. If the amount of the element or compound containing the element is less than 0.01 mass %, the concentration of active sites of the catalyst is relatively low and, therefore, a sufficiently high catalytic activity which is practically acceptable cannot be obtained and such an amount is not preferred. On the other hand, if the amount exceeds 150 mass %, the effect of the carrier cannot be exhibited sufficiently, and such an amount is not preferred.

The amount of the element or compound containing the element is more preferably from 0.05 to 100 mass %, more preferably from 0.1 to 90 mass %, particularly from 0.3 to 30 mass %.

Specific examples of the carrier-type catalyst for producing both end-hydroxyl group-terminated diols according to the first aspect of the present invention may include: Cr oxide-alumina, Cr oxide-silica, Cr oxide-silica alumina, Cu oxide-alumina, Cu oxide-silica, Mo oxide-alumina, Mo oxide-silica, Re-alumina, Re-silica, Re-activated carbon, Co-diatomaceous earth, Co-alumina, Co-silica, Co-silica alumina, Co-carbon, Ni-diatomaceous earth, Ni-alumina, Ni-silica, Ni-silica alumina, Ni-carbon, Ni-Cu-alumina, Ru-alumina, Ru-silica, Ru-silica alumina, Ru-carbon, Pd-alumina, Pd-silica, Pd-silica alumina, Pd-carbon, Pd-barium sulfate, Pd-calcium carbonate, Pt-alumina, Pt-silica, Pt-silica alumina, Pt-carbon, etc. These catalyst may be used individually or in combination of two or more species thereof.

Among the catalysts for producing both end-hydroxyl group-terminated diols according to the first aspect of the present invention, the heterogeneous catalyst may most preferably be a sponge-type or carrier-type catalyst containing at least one element selected from the group consisting of Fe, Co, Ni, CU, Re and Ru, and/or a compound containing at least one of these elements.

The shape, form, size, etc., of these catalysts are not particularly limited. Specific examples of the shape or form of the catalyst may include: powder-type, solid ground or crushed product-type, flake-type, spherical molded article-type, columnar molded article-type and circular molded article-type. With respect to the size of the catalyst, it is possible to use a catalyst having an average particle size of 1 to 1,000 μm, preferably about 10 to 200 μm, in the case of the suspension or fluidized bed-type reaction. In the case of the fixed bed-type reaction, it is possible to use a catalyst having an average particle size of about 1 to 20 mm, preferably 3 to 15 mm.

In the case of the suspension or fluidized bed-type reaction, if the average particle size of catalyst is less than the above-described range (i.e., 1 to 1,000 μm), there can be caused difficulty in separating the catalyst after the reaction. On the other hand, if the particle size exceeds this range (i.e., 1 to 1,000 μm), it is possible that the reaction is not conducted efficiently due to the precipitation of the catalyst. In the case of a fixed bed-type reaction, if the average particle size is less than the above-described range (i.e., about 1 to 20 mm), clogging or plugging of the catalyst layer or an increase in the differential pressure is liable to occur. On the other hand, if the particle size exceeds this range (i.e., about 1 to 20 mm), the surface area of the catalyst per the unit volume of a reactor is liable to decrease and this can disadvantageously cause a reduction in the reaction efficiency.

Among the catalysts for producing both end-hydroxyl group-terminated diols according to the first aspect of the present invention, the shape or form and the particle size of the heterogeneous catalyst may appropriately be selected in view of the suitability for the reaction type.

(Production Process for Catalyst)

The second aspect of the present invention is described below. The second aspect of the present invention relates to a process for producing the catalyst for producing both end-hydroxyl group-terminated diols according to the first aspect of the present invention.

The process for producing the catalyst for producing both end-hydroxyl group-terminated diols according to the second aspect of the present invention may be conducted by selecting an optimal method in view of the catalyst for producing both end-hydroxyl group-terminated dials, which is to be produced in this process. In the preparation of this catalyst, it is possible to use any of those processes which, per se, are known in the art.

In a case where the catalyst for producing both end-hydroxyl group-terminated diols is a sponge-type catalyst or a carrier-type catalyst, each of these catalysts can be produced by a production process comprising the following steps. Of course, in the present invention, the production process for the catalyst is not limited to these specific processes, but the catalysts may be produced by any of those processes which, per se, are known in the art.

For example, the sponge-type catalyst can be produced by a production process comprising the following Step (A) and Step (B):

Step (A); a step of producing an alloy of aluminum and at least one element selected from the group consisting of Group V elements, Group VI elements, Group VII elements, Group VIII elements, Group IX elements, Group X elements, and Group XI elements in the periodic table;

Step (B): a step of eluting aluminum from the alloy obtained in Step (A), to thereby produce a catalyst for producing both end-hydroxyl group-terminated diols.

The carrier-type catalyst can be produced by a production process comprising the following Step (C) and Step (D):

Step (C): a step of causing at least one element or a compound containing the at least one element to be carried on a carrier, the element being selected from the group consisting of Group V elements, Group VI elements, Group VII elements, Group VIII elements, Group IX elements, Group X elements, and Group XI elements in the periodic table, to thereby produce a carrier carrying thereon the at least one element;

Step (D): a step of hydrogenating the at least one element carried on the carrier obtained in Step (C), to thereby produce a catalyst for producing both end-hydroxyl group-terminated diols.

Further, with respect to the catalysts other than the sponge-type catalyst and the carrier-type catalyst, for example, a metal-type catalyst can be produced by a process wherein a salt, an oxide, a hydroxide, etc., of a metal is treated with a reducing agent such as hydrogen. An oxide or hydroxide catalyst can be produced by a process wherein a metal hydroxide or oxide is precipitated by using an alkali, etc., in a metal salt solution, or a method wherein the resultant precipitate is calcined. A boride catalyst can be produced by a process wherein a metal salt is treated with tetrahydroborate. Further, a phosphide catalyst can be produced by a process wherein a metal solution is treated with a phosphite.

In the case of carrier-type catalyst, examples of the production process may include: in addition to the above-describe production processes, a method wherein a hydroxide or oxide of a metal is deposited on a carrier, and the resultant carrier is calcined; a method wherein a carrier is impregnated with a metal salt solution, and the resultant carrier is calcined; a method wherein a carrier having thereon a deposited metal hydroxide or oxide, or a carrier impregnated with a metal salt solution is calcined and then is reduced with a reducing agent, to thereby prepare a catalyst.

In any case, the second aspect of the present invention is not limited to the above-mentioned specific processes, but any process may be used as long as it can produce the catalyst for producing both end-hydroxyl group-terminated diols according to the first aspect of the present invention.

(Production Process for Both End-Hydroxyl Group-Terminated Diol)

The third aspect of the present invention is described below. The third aspect of the present invention relates to a process for producing both end-hydroxyl group-terminated diols, wherein an epoxy alcohol represented by the following general formula (1) is subjected to a hydrogenolysis reaction in the presence of a catalyst for producing both end-hydroxyl group-terminated diols according to any of claims 1-5, in the presence of at least one solvent selected from the group consisting of ethers, esters, aromatic hydrocarbon compounds, alicyclic hydrocarbon compounds and aliphatic hydrocarbon compounds, to thereby obtain a both end-hydroxyl group-terminated diol represented by the following general formula (2).

General Formula (1):

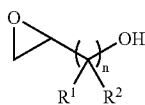

(wherein $R^1$ and $R^2$ each independently represents hydrogen, an alkyl group having 1 to 8 carbon atoms, a cycloalkyl group having 3 to 10 carbon atoms, or an aryl group having 6 to 13 carbon atoms and n represents an integer of 1 to 6);

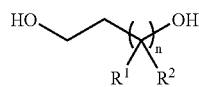

(wherein $R^1$ and $R^2$ each independently represents hydrogen, an alkyl group having 1 to 8 carbon atoms, a cycloalkyl group having 3 to 10 carbon atoms, or an aryl group having 6 to 13 carbon atoms and n represents an integer of 1 to 6).

(Epoxy Alcohol)

The compound represented by the general formula (1) to be used in the process for producing both end-hydroxyl group-terminated diols according to the third aspect of the present invention is an epoxy alcohol compound. More specifically, the compound represented by the general formula (1) may include; a compound where a mono-substituted oxirane ring and a hydroxyl group are bonded through a methylene chain having 1 to 6 carbon atoms, or a methylene chain having 1 to 6 carbon atoms which has been substituted with a cycloalkyl group, an aryl group or an alkyl group having 1 to 8 carbon atoms.

Specific examples of the epoxy alcohol compound may include: glycidol, 3,4-epoxy-2-butanol, 1,2-epoxy-3-pentanol, 1,2-epoxy-3-hexanol, 1,2-epoxy-3-heptanol, 2-methyl-3,4-epoxy-2-butanol, 1-phenyl-2,3-epoxy-1-propanol, 1-cyclohexyl-2,3-epoxy-1-propanol, 3,4-epoxy-1-butanol, 4,5-epoxy-1-pentanol, 5,6-epoxy-1-hexanol and 7,8-epoxy-1-octanol. However, the epoxy alcohol compounds usable in the present invention are not limited to these specific compounds.

Among these, glycidol, 3,4-epoxy-1-butanol and 3,4-epoxy-2-butanol are preferred in view of easy availability thereof, the industrial value of the both end-hydroxyl group-terminated diol as the reaction product, etc.

(Solvent)

The process for producing both end-hydroxyl group-terminated diols according to the third aspect of the present invention has a purpose of producing the both end-hydroxyl group-terminated diols with a high selectivity by the regioselective (or regiospecific) hydrogenolysis reaction of the epoxy ring of an epoxy alcohol and is characterized in that the reaction is conducted by using a solvent having a low polarity.

As described above, conventionally reported hydrogenolysis reactions of an epoxy alcohol have been conducted in a solvent having a hydroxyl group, such as water or alcohol, However, the use of such a polar solvent causes, as a side reaction, a ring-opening reaction of the epoxy ring due to the solvent molecule. Therefore, the known reaction can disadvantageously decrease the hydrogenolysis selectivity corresponding to the conversion of the epoxy alcohol into a hydroxyl group-terminated alcohol which is intended to be obtained.

As a result of the present inventors, study, it has been found that when a low-polarity solvent having no hydroxyl group is used, not only the ring-opening reaction of the epoxy ring due to the solvent molecule, which is a side reaction, is not substantially produced, but also the regioselectivity of the hydroxyl group provided by the ring opening of the epoxy ring is elevated, that is, the ratio of the hydroxyl group-terminated alcohol to be produced is increased, so that such a process is advantageous as the process for producing the both end-hydroxyl group-terminated diols. According to the present inventors, investigation, it is presumed that the reason why the selectivity is increased by the use of a low-polarity solvent is that, when a low-polarity solvent is used, the interaction between the solvent molecule and the hydroxyl group of the epoxy alcohol is decreased and reversely the hydroxyl group is oriented toward the catalyst surface side. The steric relationship provided by such an orientation seems to function advantageously for producing the both end-hydroxyl group-terminated diols, in view of the interaction between the catalyst active site and the oxygen atom of the epoxy ring. At the present stage, however, the details of such a phenomenon are not necessarily clear.

Further, in the process for producing the both end-hydroxyl group-terminated diols according to the third aspect of the present invention, the use of a solvent is preferred also in view of the control of the ring-opening reaction of the epoxy ring due to dilution therewith, the removal of the heat of reaction, or prevention of a decrease in the hydrogen diffusion efficiency which can be caused due to an increase in the viscosity of the reaction system.

(Examples of Solvent)

Specific examples of the solvent usable in the process for producing the both end-hydroxyl group-terminated diols according to the third aspect of the present invention may include: ether solvents such as diethyl ether, dipropyl ether, diisopropyl ether, dibutyl ether, ethylene glycol dimethyl ether, ethylene glycol diethyl ether, ethylene glycol dibutyl ether, diethylene glycol dimethyl ether, diethylene glycol diethyl ether, diethylene glycol dibutyl ether, tetrahydrofuran and 1,4-dioxane;

aromatic hydrocarbon solvents such as benzene, toluene and xylene;

alicyclic hydrocarbon solvents such as cyclohexane and methylcyclohexane;

aliphatic hydrocarbon solvents such as pentane, hexane, heptane and octane;

ester solvents such as methyl formate, ethyl formate, butyl formate, methyl acetate, ethyl acetate, propyl acetate, isopropyl acetate and butyl acetate; and halogenated hydrocarbon solvents such as dichloromethane, chloroform and 1,2-dichloroethane.

These solvents may be used individually or as a mixed solvent of two or more species thereof.

Among these, in view of the selectivity for the both end-hydroxyl group-terminated diols in the hydrogenolysis reaction in the process according to the third aspect of the present invention and the simple and easy availability and easy handleability, it is preferred to use diethyl ether, dibutyl ether, ethylene glycol dimethyl ether, ethylene glycol diethyl ether, 1,4-dioxane, benzene, toluene, xylene, cyclohexane, hexane, ethyl acetate, propyl acetate, isopropyl acetate and butyl acetate. It is more preferred to use diethyl ether, ethylene glycol dimethyl ether, 1,4-dioxane, toluene, cyclohexane, hexane and ethyl acetate.

In the third aspect of the present invention, the amount of the solvent to be used is not particularly limited. In general, the solvent may be used in such a range that the concentration of the epoxy alcohol as a reactant becomes 1 to 100 mass %, based on the mass of the epoxy alchol as a reactant toward the sum the epoxy alchol as a reactant and the solvent. If the epoxy alcohol concentration is less than 1 mass %, a practically acceptable reaction rate is less liable to be obtained, or the load for the separation and purification of the product from the reaction mixture containing the solvent becomes heavier, and therefore such an amount of the solvent may be disadvantageous. On the other hand, if the epoxy alcohol concentration exceeds 100 mass %, it is possible that the effect of the solvent is not fully exhibited and therefore such an amount may be disadvantageous. The epoxy alcohol concentration may preferably be 3 to 100 mass %, more preferably from 5 to 100 mass %.

(Hydrogenolysis Reaction)

In the third aspect of the present invention, the hydrogenolysis reaction of the epoxy alcohol can be conducted by contacting the epoxy alcohol with hydrogen in the presence of a catalyst. As the reaction type, it is possible to use any of known reaction types to be used for hydrogenolysis reaction or hydrogenation reaction, such as continuous-type reaction or batch-type reaction. The catalyst to be used in this embodiment may be either a homogenous catalyst or a heterogeneous catalyst. The form of the catalyst is not particularly limited and an appropriate form may be selected depending on the type of the reaction.

Specific examples of the reaction type to be used in the third aspect of the present invention may include: in the case of a homogeneous catalyst, a simple stirring tank, a bubble tower-type reaction tank and a tubular reaction tank. Specific examples of the reaction type may include; in the case of a heterogeneous catalyst, a suspension-bed simple stirring tank, a fluidized-bed bubble tower-type reaction tank, a fluidized-bed tubular reaction tank, a fixed-bed liquid phase flow-system tubular reaction tank, and a fixed-bed trickle bed-system tubular reaction tank. However, the reaction types usable in the present invention are not limited to these specific reaction types.

In the process for producing the both end-hydroxyl group-terminated diols according to the third aspect of the present invention, the amount of the catalyst to be used for the hydrogenolysis reaction varies depending on the reaction type and is not particularly limited. For example, in the case of batch reaction, the amount of the homogeneous catalyst used may usually be 0.001 to 10 mass %, preferably 0.01 to 5 mass %, more preferably 0.01 to 3 mass %, based on the reactant epoxy alcohol solution. The amount of the heterogeneous catalyst to be used may usually be 0.01 to 100 mass %, preferably 0.1 to 70 mass %, more preferably 0.1 to 50 mass %, based on the reactant epoxy alcohol compound.

If the amount of the catalyst is small, a practically sufficient reaction rate may not be obtained. On the other hand, if the amount of the catalyst is large, a reduction in the reaction yield or an increase in the catalyst cost may undesirably be provided due to an increase in the occurrence of the side reaction.

In the process for producing the both end-hydroxyl group-terminated diols according to the third aspect of the present invention, the hydrogen pressure at the hydrogenolysis reaction is not particularly limited. The reaction may be conducted either under atmospheric pressure condition or under a pressurized condition. In order to efficiently promote the reaction, the reaction may preferably be conducted under a pressurized condition. The pressure, in terms of the gauge pressure, may usually be in the range of 0 to 50 MPa, preferably 0 to 40 MPa, more preferably 0 to 30 MPa.

In the third aspect of the present invention, the hydrogenolysis reaction may be conducted at any temperature within a range such that it does not substantially decrease the reaction efficiency due to the catalyst. The reaction may usually be conducted at 0 to 200° C., preferably 0 to 180° C. and more preferably 0 to 150° C. If the reaction temperature is less than 0° C., the hydrogenolysis reaction may not proceed at a practically acceptable reaction rate. On the other hand, if the temperature exceeds 200° C., the ring opening reaction of the epoxy ring in the epoxy alcohol compound represented by the general formula (1) is more liable to proceed due the reaction of the starting material epoxy alcohol compounds represented by the general formula (1) with each other, or the reaction between the product both end-hydroxyl group-terminated diol compound represented by the general formula (2) and the epoxy alcohol compound, so that undesired by-products may be disadvantageously produced.

(Epoxy Alcohol)

The epoxy alcohol compound represented by the general formula (1) to be used in the process for producing the both end-hydroxyl group-terminated diols according to the third aspect of the present invention may one which has been prepared by any method.

General Formula (1):

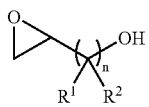

(wherein $R^1$ and $R^2$ each independently represents hydrogen, an alkyl group having 1 to 8 carbon atoms, a cycloalkyl group having 3 to 10 carbon atoms, or an aryl group having 6 to 13 carbon atoms and n represents an integer of 1 to 6).

Specific examples of the reaction for obtaining the epoxy alcohol compound represented by the general formula (1) may include: a preparation process wherein an unsaturated alcohol is epoxidized (examined Japanese Patent publication (JP-B) Sho. 51-18407); a process wherein an epoxy alcohol is prepared through the hydrolysis of an epichlorohydrin to produce monochlorohydrin and subsequently the resultant monochlorohydrin is subjected to a ring-closing reaction (*Journal of American Chemical Society*, Vol. 52, page 1521 (1930)); a preparation process wherein the carbon-carbon double bond of acrolein is opoxidized and the aldehyde group thereof is hydrogenated (U.S. Pat. No. 3,041,356); and a preparation process using transesterification between glycidyl esters and alcohols (JP-A Hei. 50-126609). Of course, the reaction for obtaining the epoxy alcohol compound usable in the present invention is not limited to these specific processes.

Among these production processes, the epoxy alcohol compound represented by the general formula (1) to be used in the process for producing the both end-hydroxyl group-terminated diols according to the third aspect of the present invention may preferably be an epoxy alcohol compound which has been obtained by the epoxidation reaction of an unsaturated alcohol, in view of the industrial importance or in view of a lower possibility of contamination due to industrially undesired impurities (such as chlorine-containing compound and aldehyde compound) which can function as a poisoning substance to the catalyst for the hydrogenation reaction.

The epoxy alcohol compound represented by the general formula (1) to be used in the third aspect of the present invention may preferably be an epoxy alcohol compound represented by the general formula (1) which has been obtained by the epoxidation reaction of an unsaturated alcohol compound represented by formula (3):

General Formula (3):

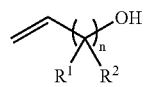

(wherein $R^1$ and $R^2$ each independently represents hydrogen, an alkyl group having 1 to 8 carbon atoms, a cycloalkyl group having 3 to 10 carbon atoms, or an aryl group having 6 to 13 carbon atoms and n represents an integer of 1 to 6).

Specific examples of the unsaturated alcohol represented by formula (3) may include: allyl alcohol, 3-buten-1-ol and 3-buten-2-ol. However, the unsaturated alcohols usable in the present invention are not limited to these specific compounds.

In a case where the epoxy alcohol compound represented by the general formula (1) which has been obtained by the epoxidation reaction of an unsaturated alcohol compound represented by formula (3) is used in the process for producing the both end-hydroxyl group-terminated diols according to the third aspect of the present invention, it is naturally possible that after the epoxidation reaction of an unsaturated alcohol compound, the produced epoxy alcohol is subjected to separation and purification by an operation such as distillation, and the thus obtained purified epoxy alcohol is used as the starting material for the hydrogenolysis reaction. In addition, it is also possible that the reaction mixture containing the epoxy alcohol compound which has been obtained by the epoxidation reaction of the unsaturated alcohol compound is used as the starting material as it is (i.e., substantially without purification), and the resultant reaction mixture is subjected to hydrogenolysis reaction so as to provide the both end-hydroxyl group-terminated diol.

In the above-described third aspect of the present invention, e.g., when 1,3-propanediol is produced from glycidol, the product glycidol may be obtained at a conversion (rate) for the glycidol of 60% or more under a desirable condition, and 70% to 100% under a more desirable condition. In this case, the selectivity factor for the 1,3-propanediol may be 60% or more under a desirable condition.

Herein, the conversion X and selectivity factors S are defined in the following manner.

Conversion X=(Moles of reacted reactant in raw material)/(moles of reactant in raw material)

Selectivity factor S=(Moles of reactant which has been obtained by calculating moles of intended product in terms of reactant)/(moles of reacted reactant)

(Both End-Hydroxyl Group-Terminated Diol)

The fourth aspect of the present invention is described below. The fourth aspect of the present invention relates to a both end-hydroxyl group-terminated diol which has been produced by the process for producing the both end-hydroxyl group-terminated diols according to the third aspect of the present invention.

In the process for producing the both end-hydroxyl group-terminated diols according to the third aspect of the present invention, the diol has been obtained by the hydrogenolysis reaction of an epoxy alcohol, and therefore, the product both end-hydroxyl group-terminated diol contains substantially no carbonyl compound as an impurity. Accordingly, the both end-hydroxyl group-terminated diol according to the fourth aspect of the present invention can provide an effect such that when polyester, etc., is produced by using such a diol, the generation of coloring or malodor attributable to the carbonyl compound can be suppressed to a low level.

For example, whether a carbonyl compound is contained in the both end-hydroxyl group-terminated diol can be confirmed by the following methods:

1) the quantitative determination of known carbonyl compounds using gas chromatography, liquid chromatography or gas chromatography/mass spectrometry;

2) the confirmation of stretching vibration peak of C=O in the vicinity of 1,600 to 1,800 $cm^{-1}$ using IR spectrum; or 3) the quantitative determination (ASTM E411-70) of a solution containing a condensation product from the carbonyl compound and 2,4-dinitrophenylhydrazine, using the visible-ray spectrum.

In the present invention, the amount of the carbonyl compound in the obtained product may preferably be less than 500 ppm, more preferably less than 100 ppm. The amount of the carbonyl compound may be measured, e.g., by qualitative determination according to ASTM E411-70 wherein a solution of the condensation product between the carbonyl compound and 2,4-dinitrophenyl hidrazine is qualitatively analysed by using the visible spectrum, etc.

EXAMPLES

Hereinbelow, the present invention will be described in more detail with reference to Examples and Comparative Examples. Of course, the present invention are not limited to these specific Examples.

In the following Examples, each of reactions was analyzed by using gas chromatography (hereinafter simply referred to as "GC") under the following conditions.

GC Analysis Conditions
  Apparatus: GC-17A (mfd. by Shimadzu Corporation)
  Column: FFAP, inside diameter 0.25 mm$\phi$×length 30 m (mfd. by J&W Co.)
  Carrier gas: He 1 ml/min, split ratio: 1/30
  Detector; FID (Hydrogen flame ionization detector)
  Column temperature: (temperature increasing conditions) Retention at 40° C. for ten minutes, thereafter temperature increase at a rate of 10° C./minute to 200° C., and then retention at 200° C. for 25 minutes
  Injection temperature: 230° C.
  Amount of injected sample: 0.2 µl Example 1

2.0 g of sponge-Ni catalyst (trade name: R-200, mfd. by Nikko Rika K.K.) wetted with water was transferred to an autoclave made of stainless steel (mfd. by Taiatsu Glass K.K.) equipped with a stirrer and having an internal volume of 120 ml, then 20 ml of methanol was added to the catalyst and thoroughly mixed under shaking. Thereafter, the resultant supernatant was removed from the autoclave by decantation. This operation was further repeated twice, and then the same operation was conducted three times except for using 20 ml of dioxane in place of methanol to effect the solvent replacement. The resultant supernatant which had finally been obtained was removed from the catalyst by decantation, and thereafter, 30 g of dioxane and 5.00 g of glycidol were added thereto.

The reactor (vessel) was tightly closed and an operation of pressurizing the inside of the autoclave to 1.0 MPa (gauge pressure) with nitrogen and then depressurizing the inside of the autoclave to 0.0 MPa (gauge pressure) was repeated 5 times to replace the air in the autoclave with nitrogen. Further, the nitrogen was replaced with hydrogen by the same operation, and a hydrogen pressure of 0.8 MPa (gauge pressure) was finally applied to the autoclave. Subsequently, while the contents of the autoclave were being stirred at 400 rpm, the temperature in the autoclave was elevated and the reaction was conducted at 80° C. for 5 hours. During the reaction, hydrogen was introduced into the autoclave so as to maintain the reaction pressure at a constant level.

When the reaction was completed, the reactor was cooled to room temperature and depressurized, and the contents of the autoclave were replaced with nitrogen, and the reactor was opened. Thereafter, the supernatant was removed from the autoclave and the supernatant was analyzed by GC.

As a result of the calculation from the peak area ratios between the respective peaks appearing in the resultant GC chart, the conversion of glycidol was 76.6%, the selectivity for 1,3-propanediol was 57.6% and the selectivity for 1,2-propanediol was 41.3%. Further, according to the GC analysis, peaks corresponding to 3-hydroxypropionaldehyde, hydroxyacetone and propionaldehyde as carbonyl compounds were not detected.

Example 2

2.0 g of sponge-Ni catalyst (trade name: R-200, mfd. by Nikko Rika K.K.) wetted with water was transferred to an autoclave made of stainless steel (Mfd. by Taiatsu Glass K.K.) equipped with a stirrer and having an internal volume of 120 ml, then 20 ml of ethanol was added to the catalyst and thoroughly mixed under shaking. Thereafter, the resultant supernatant was removed from the autoclave by decantation. This operation was further repeated twice, and then the same operation was conducted three times except for using 20 ml of cyclohexane in place of ethanol to effect the solvent replacement. The resultant supernatant which had finally been obtained was removed from the catalyst by decantation, and thereafter, 30 g of cyclohexane and 5.00 g of glycidol were added thereto.

The reactor was tightly closed, and then the contents (atmosphere) of the autoclave were replaced with nitrogen, and further with hydrogen sequentially in the same manner as in Example 1, and a hydrogen pressure of 0.8 MPa (gauge pressure) was finally applied to the autoclave. Subsequently, while the contents of the autoclave were being stirred at 400 rpm, the temperature in the autoclave was elevated and the reaction was conducted at 80° C. for 5 hours. During the reaction, hydrogen was introduced into the autoclave so as to maintain the reaction pressure at a constant level.

When the reaction was completed, the reactor was cooled to room temperature and depressurized, and the contents of the autoclave were replaced with nitrogen, and then the reactor was opened. Thereafter, the supernatant was removed from the autoclave and the supernatant was analyzed by GC.

As a result of the calculation from the peak area ratios between the respective peaks appearing in the resultant GC chart, the conversion of glycidol was 100%, the selectivity for 1,3-propanediol was 30.8% and the selectivity for 1,2-propanediol was 41.3%. Further, according to the GC analysis, peaks corresponding to 3-hydroxypropionaldehyde, hydroxyacetone and propionaldehyde as carbonyl compounds were not detected.

Example 3

2.0 g of sponge-Ni catalyst (trade name: R-200, mfd. by Nikko Rika K.K.) wetted with water was transferred to an autoclave made of stainless steel (mfd. by Taiatsu Glass K.K.) equipped with a stirrer and having an internal volume of 120 ml, then 20 ml of ethanol was added to the catalyst and thoroughly mixed under shaking. Thereafter, the resultant supernatant was removed from the autoclave by decantation. This operation was further repeated twice, and then the same operation was conducted three times except for using 20 ml of 1,2-dimethoxyethane in place of ethanol to effect the solvent replacement. The resultant supernatant which had finally been obtained was removed from the catalyst by decantation, and thereafter, 30 g of 1,2-dimethoxyethane and 5.00 g of glycidol were added thereto.

The reactor was tightly closed, and then the contents (atmosphere) of the autoclave were replaced with nitrogen, and further with hydrogen sequentially in the same manner as in Example 1, and a hydrogen pressure of 0.8 MPa (gauge pressure) was finally applied to the autoclave. Subsequently, while the contents of the autoclave were being stirred at 400 rpm, the temperature in the autoclave was elevated and the reaction was conducted at 80° C. for 5 hours. During the reaction, hydrogen was introduced into the autoclave so as to maintain the reaction pressure at a constant level.

When the reaction was completed, the reactor was cooled to room temperature and depressurized, and the contents of the autoclave were replaced with nitrogen, and then the reactor was opened. Thereafter, the supernatant was removed from the autoclave and the supernatant was analyzed by GC.

As a result of the calculation from the peak area ratios between the respective peaks appearing in the resultant GC chart, the conversion of glycidol was 91.7%, the selectivity for 1,3-propanediol was 40.4% and the selectivity for 1,2-propanediol was 46.6%. Further, according to the GC analysis, peaks corresponding to 3-hydroxypropionaldehyde, hydroxyacetone and propionaldehyde as carbonyl compounds were not detected.

Comparative Example 1

2.0 g of sponge-Ni catalyst (trade name: R-200, mfd. by Nikko Rika K.K.) wetted with water was transferred to an autoclave made of stainless steel (mfd. by Taiatsu Glass K.K.) equipped with a stirrer and having an internal volume of 120 ml, and then the resultant supernatant was removed from the autoclave by decantation. Thereafter, 20 g of water and 5.24 g of glycidol were added to the wetted catalyst.

The reactor was tightly closed, and then the contents (atmosphere) of the autoclave were replaced with nitrogen, and further with hydrogen sequentially in the same manner as in Example 1, and a hydrogen pressure of 0.8 MPa (gauge pressure) was finally applied to the autoclave. Subsequently, while the contents of the autoclave were being stirred at 400 rpm, the temperature in the autoclave was elevated and the reaction was conducted at 60° C. for 5 hours. During the reaction, hydrogen was introduced into the autoclave so as to maintain the reaction pressure at a constant level.

When the reaction was completed, the reactor was cooled to room temperature and depressurized, and the contents of the autoclave were replaced with nitrogen, and then the reactor was opened. Thereafter, the supernatant was removed from the autoclave and the supernatant was analyzed by GC.

As a result of the calculation from the peak area ratios between the respective peaks appearing in the resultant GC chart, the conversion of glycidol was 88.6%, the selectivity for 1,3-propanediol was 9.9% and the selectivity for 1,2-propanediol was 71.9%. Further, according to the GC analysis, peaks corresponding to 3-hydroxypropionaldehyde, hydroxyacetone and propionaldehyde as carbonyl compounds were not detected.

As described above, based on the comparison between the results obtained in Examples 1 to 3 and Comparative Example 1, it may be understood that when the hydrogenolysis reaction of glycidol is conducted in a water solvent, the selectivity for 1,3-propanediol was extremely low. On the contrary, when a solvent having a lower polarity is used, the selectivity for 1,3-propanediol can remarkably be increased.

Example 4

Preparation of Sponge-Co Catalyst

In a 50 ml-volume glass beaker, 1.3 g of sodium hydroxide was dissolved in 10.9 g of water and, to the resultant solution, 1.0 g of sponge-Co (Co content: 50 mass %, mfd. by Wako Pure Chemical Industries, Ltd.) was gradually added over 10 minutes while the mixture was being stirred with a magnetic stirrer. After the addition of the sponge-Co, the glass beaker was immersed in a hot water bath and the reaction was conducted at 50° C. for another 1 hour.

The resultant supernatant was removed from the glass beaker by decantation, 20 ml of water was added to the resultant catalyst. The resultant mixture was stirred, and thereafter, the supernatant was removed from the glass beaker. This water washing operation was repeated until the pH of the supernatant reached 7 to thereby prepare a sponge-Co catalyst suspended in water.

Example 5

The sponge-Co catalyst wetted with water, which had been prepared in Example 4 was transferred to an autoclave made of stainless steel (mfd. by Taiatsu Glass K.K.) equipped with a stirrer and having an internal volume of 120 ml, then 20 ml of ethanol was added to the catalyst and thoroughly mixed under shaking. Thereafter, the resultant supernatant was removed from the autoclave by decantation. This operation was further repeated twice, and then the same operation was conducted three times except for using 20 ml of 1,4-dioxane in place of ethanol to effect the solvent replacement. The resultant supernatant which had finally been obtained was removed from the catalyst by decantation, and thereafter, 30 g of 1,4-dioxane and 5.00 g of glycidol were added thereto.

The reactor was tightly closed, and then the contents (atmosphere) of the autoclave were replaced with nitrogen, and further with hydrogen, sequentially, in the same manner as in Example 1, and a hydrogen pressure of 0.8 MPa (gauge pressure) was finally applied to the autoclave. Subsequently, while the contents of the autoclave were being stirred at 400 rpm, the temperature in the autoclave was elevated and the reaction was conducted at 80° C. for 5 hours. During the reaction, hydrogen was introduced into the autoclave so as to maintain the reaction pressure at a constant level.

When the reaction was completed, the reactor was cooled to room temperature and depressurized, and the contents of the autoclave were replaced with nitrogen, and then the reactor was opened. Thereafter, the supernatant was removed from the autoclave and the supernatant was analyzed by GC.

As a result of the calculation from the peak area ratios between the respective peaks appearing in the resultant GC chart, the conversion of glycidol was 95.4%, the selectivity for 1,3-propanediol was 50.6% and the selectivity for 1,2-propanediol was 6.0%. Further, according to the GC analysis, peaks corresponding to 3-hydroxypropionaldehyde, hydroxyacetone and propionaldehyde as carbonyl compounds were not detected.

Example 6

30.2 g of dimethoxyethane was placed in an autoclave made of stainless steel (mfd. by Taiatsu Glass K.K.) equipped with a stirrer and having an internal volume of 120 ml, then 5.0 g of glycidol was added thereto, and thereafter, 0.50 g of 5% Ru-carbon catalyst (mfd. by NE Chemcat K.K.) was gradually added to the autoclave.

The reactor was tightly closed, and then the contents (atmosphere) of the autoclave were replaced with nitrogen, and further with hydrogen sequentially in the same manner as in Example 1, and a hydrogen pressure of 0.8 MPa (gauge pressure) was finally applied to the autoclave. Subsequently, while the contents of the autoclave were being stirred at 400 rpm, the temperature in the autoclave was elevated and the reaction was conducted at 100° C. for 5 hours. During the reaction, hydrogen was introduced into the autoclave so as to maintain the reaction pressure at a constant level.

When the reaction was completed, the reactor was cooled to room temperature and depressurized, and the contents of the autoclave were replaced with nitrogen, and then the reactor was opened. Thereafter, the supernatant was removed from the autoclave and the supernatant was analyzed by GC.

As a result of the calculation from the peak area ratios between the respective peaks appearing in the resultant GC chart, the conversion of glycidol was 50.7%, the selectivity for 1,3-propanediol was 19.5% and the selectivity for 1,2-propanediol was 5.1%. Further, according to the GC analysis, peaks corresponding to 3-hydroxypropionaldehyde, hydroxyacetone and propionaldehyde as carbonyl compounds were not detected.

Example 7

2.0 g of sponge-Ni catalyst (trade name: R-200, mfd. by Nikko Rika K.K.) wetted with water was transferred to an autoclave made of stainless steel (mfd. by Taiatsu Glass K.K.) equipped with a stirrer and having an internal volume of 120 ml, then 20 ml of methanol was added to the catalyst and thoroughly mixed under shaking. Thereafter, the resultant supernatant was removed from the autoclave by decantation. This operation was further repeated twice, and then the same operation was conducted three times except for using 20 ml of 1,2-dimethoxyethane in place of ethanol to effect the solvent replacement. The resultant supernatant which had finally been obtained was removed from the catalyst by decantation, and thereafter, 30 g of 1,2-dimethoxyethane and 5.00 g of glycidol were added thereto.

The reactor was tightly closed, and then the contents (atmosphere) of the autoclave were replaced with nitrogen, and further with hydrogen, sequentially, in the same manner as in Example 1, and a hydrogen pressure of 0.8 MPa (gauge pressure) was finally applied to the autoclave. Subsequently, while the contents of the autoclave were being stirred at 400 rpm, the temperature in the autoclave was elevated and the reaction was conducted at 80° C. for 5 hours. During the reaction, hydrogen was introduced into the autoclave so as to maintain the reaction pressure at a constant level.

When the reaction was completed, the reactor was cooled to room temperature and depressurized, and the contents of the autoclave were replaced with nitrogen, and then the reactor was opened. Thereafter, the supernatant was removed from the autoclave and the supernatant was analyzed by GC.

As a result of the calculation from the peak area ratios between the respective peaks appearing in the resultant GC chart, the conversion of glycidol was 81.4%, the selectivity for 1,3-propanediol was 61.1% and the selectivity for 1,2-propanediol was 2.9%. Further, according to the GC analysis, peaks corresponding to 3-hydroxypropionaldehyde, hydroxyacetone and propionaldehyde as carbonyl compounds were not detected.

Example 8

2.0 g of sponge-Ni catalyst (trade name: R-200, mfd. by Nikko Rika K.K.) wetted with water was transferred to an autoclave made of stainless steel (mfd. by Taiatsu Glass K.K.) equipped with a stirrer and having an internal volume of 120 ml, then 20 ml of ethanol was added to the catalyst and thoroughly mixed under shaking. Thereafter, the resultant supernatant was removed from the autoclave by decantation. This operation was further repeated twice to effect the solvent replacement. The resultant supernatant which had finally been obtained was removed from the catalyst by decantation, and thereafter, 30 g of ethanol and 5.00 g of glycidol were added thereto.

The reactor was tightly closed, and then the contents (atmosphere) of the autoclave were replaced with nitrogen, and further with hydrogen, sequentially, in the same manner as in Example 1, and a hydrogen pressure of 0.8 MPa (gauge pressure) was finally applied to the autoclave. Subsequently, while the contents of the autoclave were being stirred at 400 rpm, the temperature in the autoclave was elevated and the reaction was conducted at 80° C. for 5 hours. During the reaction, hydrogen was introduced into the autoclave so as to maintain the reaction pressure at a constant level.

When the reaction was completed, the reactor was cooled to room temperature and depressurized, and the contents of the autoclave were replaced with nitrogen, and then the reactor was opened. Thereafter, the supernatant was removed from the autoclave and the supernatant was analyzed by GC.

As a result of the calculation from the peak area ratios between the respective peaks appearing in the resultant GC chart, the conversion of glycidol was 78.2%, the selectivity for 1,3-propanediol was 61.1 t and the selectivity for 1,2-propanediol was 6.9%. Further, according to the GC analysis, peaks corresponding to 3-hydroxypropionaldehyde, hydroxyacetone and propionaldehyde as carbonyl compounds were not detected.

Example 9

2.0 g of a sponge-Co catalyst (trade name: R-400, mfd. by Nikko Rika K.K.) wetted with water was transferred to an autoclave made of stainless steel (mfd. by Taiatsu Glass K.K.) equipped with a stirrer and having an internal volume of 120 ml, then 20 ml of ethanol was added to the catalyst and thoroughly mixed under shaking. Thereafter, the resultant supernatant was removed from the autoclave by decantation. This operation was further repeated twice, and then the same operation was conducted three times except for using 20 ml of dioxane in place of ethanol to effect the solvent replacement. The resultant supernatant which had finally been obtained was removed from the catalyst by decantation, and thereafter, 30 g of dioxane and 5.00 g of glycidol were added thereto.

The reactor was tightly closed, and then the contents (atmosphere) of the autoclave were replaced with nitrogen, and further with hydrogen sequentially in the same manner as in Example 1, and a hydrogen pressure of 0.8 MPa (gauge pressure) was finally applied to the autoclave. Subsequently, while the contents of the autoclave were being stirred at 400 rpm, the temperature in the autoclave was elevated and the reaction was conducted at 80° C. for 5 hours. During the reaction, hydrogen was introduced into the autoclave so as to maintain the reaction pressure at a constant level.

When the reaction was completed, the reactor was cooled to room temperature and depressurized, and the contents of the autoclave were replaced with nitrogen, and then the reactor was opened. Thereafter, the supernatant was removed from the autoclave and the supernatant was analyzed by GC.

As a result of the calculation from the peak area ratios between the respective peaks appearing in the resultant GC chart, the conversion of glycidol was 79.9%, the selectivity for 1,3-propanediol was 53.6% and the selectivity for 1,2-propanediol was 8.4%. Further, according to the GC analysis, peaks corresponding to 3-hydroxypropionaldehyde, hydroxyacetone and propionaldehyde as carbonyl compounds were not detected.

Example 10

2.0 g of a sponge-Co catalyst (trade name: R-400, mfd. by Nikko Rika K.K.) wetted with water was transferred to an autoclave made of stainless steel (mfd. by Taiatsu Glass K.K.) equipped with a stirrer and having an internal volume of 120 ml, then 20 ml of ethanol was added to the catalyst and thoroughly mixed under shaking. Thereafter, the resultant supernatant was removed from the autoclave by decantation. This operation was further repeated twice, and then the same operation was conducted three times except for using 20 ml of dioxane in place of ethanol to effect the solvent replacement. The resultant supernatant which had finally been obtained was removed from the catalyst by decantation, and thereafter, 30 g of dioxane and 5.00 g of glycidol were added thereto.

The reactor was tightly closed, and then the contents (atmosphere) of the autoclave were replaced with nitrogen, and further with hydrogen, sequentially, in the same manner as in Example 1, and a hydrogen pressure of 1.6 MPa (gauge pressure) was finally applied to the autoclave. Subsequently, while the contents of the autoclave were being stirred at 400 rpm, the temperature in the autoclave was elevated and the reaction was conducted at 80° C. for 5 hours. During the reaction, hydrogen was introduced into the autoclave so as to maintain the reaction pressure at a constant level.

When the reaction was completed, the reactor was cooled to room temperature and depressurized, and the contents of the autoclave were replaced with nitrogen, and then the reactor was opened. Thereafter, the supernatant was removed from the autoclave and the supernatant was analyzed by GC.

As a result of the calculation from the peak area ratios between the respective peaks appearing in the resultant GC chart, the conversion of glycidol was 91.2%, the selectivity for 1,3-propanediol was 57.9% and the selectivity for 1,2-propanediol was 9.1%. Further, according to the GC analysis, peaks corresponding to 3-hydroxypropionaldehyde, hydroxyacetone and propionaldehyde as carbonyl compounds were not detected.

Example 11

2.0 g of a sponge-Co catalyst (trade name: R-400, mfd. by Nikko Rika K.K.) wetted with water was transferred to an autoclave made of stainless steel (mfd. by Taiatsu Glass K.K.) equipped with a stirrer and having an internal volume of 120 ml, then 20 ml of ethanol was added to the catalyst and thoroughly mixed under shaking. Thereafter, the resultant supernatant was removed from the autoclave by decantation. This operation was further repeated twice, and then the same operation was conducted three times except for using 20 ml of dioxane in place of ethanol to effect the solvent replacement. The resultant supernatant which had finally been obtained was removed from the catalyst by decantation, and thereafter, 30 g of dioxane and 5.00 g of glycidol were added thereto.

The reactor was tightly closed, and then the contents (atmosphere) of the autoclave were replaced with nitrogen, and further with hydrogen sequentially in the same manner as in Example 1, and a hydrogen pressure of 0.8 MPa (gauge pressure) was finally applied to the autoclave. Subsequently, while the contents of the autoclave were being stirred at 800 rpm, the temperature in the autoclave was elevated and the reaction was conducted at 80° C. for 5 hours. During the reaction, hydrogen was introduced into the autoclave so as to maintain the reaction pressure at a constant level.

When the reaction was completed, the reactor was cooled to room temperature and depressurized, and the contents of the autoclave were replaced with nitrogen, and then the reactor was opened. Thereafter, the supernatant was removed from the autoclave and the supernatant was analyzed by GC.

As a result of the calculation from the peak area ratios between the respective peaks appearing in the resultant GC chart, the conversion of glycidol was 87.2%, the selectivity for 1,3-propanediol was 54.5% and the selectivity for 1,2-propanediol was 8.2%. Further, according to the GC analysis, peaks corresponding to 3-hydroxypropionaldehyde, hydroxyacetone and propionaldehyde as carbonyl compounds were not detected.

Example 12

Preparation of Co Catalyst Carried on Silica Carrier 5.480 g of cobalt nitrate hexahydrate was weighed in a beaker, and 9.00 g of deionized water was added to the beaker to thereby prepare Aqueous Solution (1). Then, 10.00 g of silica carrier (CARiACT Q-15 mfd. by Fuji Silysia Chemical LTD) was added to the beaker containing Aqueous Solution (1) which had been prepared therein, so as to cause the entire amount of Aqueous Solution (1) to be absorbed into the silica carrier.

The resultant silica carrier which had absorbed therein Aqueous Solution (1) was dried at 100° C. for one hour under a stream of nitrogen. The drying was carried out under a stream of nitrogen at a space velocity 2400 h$^{-1}$ under atmospheric pressure. Then, the silica carrier was reduced at 400° C. for two hours under a stream of hydrogen to thereby prepare a catalyst carrying metal-Co on the silica carrier. The reduction was carried out under a stream of hydrogen at a space velocity 2400 h$^{-1}$ under atmospheric pressure.

Example 13

The catalyst carrying metal-Co on the silica carrier, which had been prepared in Example 12, was transferred to an autoclave made of stainless steel (mfd. by Taiatsu Glass K.K.) equipped with a stirrer and having an internal volume of 120 ml, then 20 ml of ethanol was added to the catalyst and thoroughly mixed under shaking. Thereafter, the resultant supernatant was removed from the autoclave by decantation. This operation was further repeated twice, and then the same operation was conducted three times except for using 20 ml of 1,2-dimethoxyethane in place of ethanol to effect the solvent replacement. The resultant supernatant which had finally been obtained was removed from the catalyst by decantation, and thereafter, 30 g of 1,2-dimethoxyethane and 5.00 g of glycidol were added thereto.

The reactor was tightly closed, and then the contents (atmosphere) of the autoclave were replaced with nitrogen, and further with hydrogen, sequentially, in the same manner as in Example 1, and a hydrogen pressure of 1.6 MPa (gauge pressure) was finally applied to the autoclave. Subsequently, while the contents of the autoclave were being stirred at 800 rpm, the temperature in the autoclave was elevated and the reaction was conducted at 80° C. for 5 hours. During the reaction, hydrogen was introduced into the autoclave so as to maintain the reaction pressure at a constant level.

When the reaction was completed, the reactor was cooled to room temperature and depressurized, and the contents of the autoclave were replaced with nitrogen, and then the reactor was opened. Thereafter, the supernatant was removed from the autoclave and the supernatant was analyzed by GC.

As a result of the calculation from the peak area ratios between the respective peaks appearing in the resultant GC chart, the conversion of glycidol was 42.2%, the selectivity for 1,3-propanediol was 67.6% and the selectivity for 1,2-propanediol was 8.5%. Further, according to the GC analysis, peaks corresponding to 3-hydroxypropionaldehyde, hydroxyacetone and propionaldehyde as carbonyl compounds were not detected.

Example 14

Preparation of Co—K Catalyst Carried on Silica Carrier 5.490 g of cobalt nitrate hexahydrate and 0.021 g of potassium nitrate were weighed in a beaker, and 8.02 g of deionized water was added to the beaker to thereby prepare Aqueous Solution (2). Then, 10.00 g of silica carrier (CARiACT Q-15) was added to the beaker containing Aqueous Solution (2) which had been prepared therein, so as to cause the entire amount of Aqueous Solution (2) to be absorbed into the silica carrier.

The resultant silica carrier which had absorbed therein Aqueous Solution (2) was dried at 100° C. for one hour under a stream of nitrogen. Then, the silica carrier was reduced at 400° C. for two hours under a stream of hydrogen, to thereby prepare a catalyst carrying metal-Co on the silica carrier.

Example 15

The catalyst carrying metal-Co on the silica carrier, which had been prepared in Example 14 was transferred to an autoclave made of stainless steel (mfd. by Taiatsu Glass K.K.) equipped with a stirrer and having an internal volume of 120 ml, then 20 ml of ethanol was added to the catalyst and thoroughly mixed under shaking. Thereafter, the resultant supernatant was removed from the autoclave by decantation. This operation was further repeated twice, and then the same operation was conducted three times except for using 20 ml of 1,2-dimethoxyethane in place of ethanol to effect the solvent replacement. The resultant supernatant which had finally been obtained was removed from the catalyst by decantation, and thereafter, 30 g of 1,2-dimethoxyethane and 5.00 g of glycidol were added thereto.

The reactor was tightly closed, and then the contents (atmosphere) of the autoclave were replaced with nitrogen, and further with hydrogen sequentially in the same manner as in Example 1, and a hydrogen pressure of 1.6 MPa (gauge pressure) was finally applied to the autoclave. Subsequently, while the contents of the autoclave were being stirred at 800 rpm, the temperature in the autoclave was elevated and the reaction was conducted at 80° C. for 5 hours. During the reaction, hydrogen was introduced into the autoclave so as to maintain the reaction pressure at a constant level.

When the reaction was completed, the reactor was cooled to room temperature and depressurized, and the contents of the autoclave were replaced with nitrogen, and then the reactor was opened. Thereafter, the supernatant was removed from the autoclave and the supernatant was analyzed by GC.

As a result of the calculation from the peak area ratios between the respective peaks appearing in the resultant GC chart, the conversion of glycidol was 40.0%, the selectivity for 1,3-propanediol was 68.2% and the selectivity for 1,2-propanediol was 9.1%. Further, according to the GC analysis, peaks corresponding to 3-hydroxypropionaldehyde, hydroxyacetone and propionaldehyde as carbonyl compounds were not detected.

Example 16

Preparation of Co—Te Catalyst Carried on Silica Carrier 5.488 g of cobalt nitrate hexahydrate and 0.027 g of telluric acid were weighed in a beaker, and 8.02 g of deionized water was added to the beaker to thereby prepare Aqueous Solution (3). Then, 10.01 g of silica carrier (CARiACT Q-15) was added to the beaker containing Aqueous Solution (3) which had been prepared therein, so as to cause the entire amount of Aqueous Solution (3) to be absorbed into the silica carrier.

The resultant silica carrier which had absorbed therein Aqueous Solution (3) was dried at 100° C. for one hour under a stream of nitrogen. Then, the silica carrier was reduced at 400° C. for two hours under a stream of hydrogen, to thereby prepare a catalyst carrying metal-Co on the silica carrier.

Example 17

The catalyst carrying metal-Co on the silica carrier, which had been prepared in Example 16 was transferred to an autoclave made of stainless steel (mfd. by Taiatsu Glass K.K.) equipped with a stirrer and having an internal volume of 120 ml, then 20 ml of ethanol was added to the catalyst and thoroughly mixed under shaking. Thereafter, the resultant supernatant was removed from the autoclave by decantation. This operation was further repeated twice, and then the same operation was conducted three times except for using 20 ml of 1,2-dimethoxyethane in place of ethanol to effect the solvent replacement. The resultant supernatant which had finally been obtained was removed from the catalyst by decantation, and thereafter, 30 g of 1,2-dimethoxyethane and 5.00 g of glycidol were added thereto.

The reactor was tightly closed, and then the contents (atmosphere) of the autoclave were replaced with nitrogen, and further with hydrogen sequentially in the same manner as in Example 1, and a hydrogen pressure of 1.6 MPa (gauge pressure) was finally applied to the autoclave. Subsequently, while the contents of the autoclave were being stirred at 800 rpm, the temperature in the autoclave was elevated and the reaction was conducted at 80° C. for 5 hours. During the reaction, hydrogen was introduced into the autoclave so as to maintain the reaction pressure at a constant level.

When the reaction was completed, the reactor was cooled to room temperature and depressurized, and the contents of the autoclave were replaced with nitrogen, and then the reactor was opened. Thereafter, the supernatant was removed from the autoclave and the supernatant was analyzed by GC.

As a result of the calculation from the peak area ratios between the respective peaks appearing in the resultant GC chart, the conversion of glycidol was 52.9%, the selectivity for 1,3-propanediol was 51.9% and the selectivity for 1,2-propanediol was 7.6%. Further, according to the GC analysis, peaks corresponding to 3-hydroxypropionaldehyde, hydroxyacetone and propionaldehyde as carbonyl compounds were not detected.

Example 18

The catalyst carrying metal-Co on the silica carrier, which had been prepared in Example 12, was transferred to an autoclave made of stainless steel (mfd. by Taiatsu Glass K.K.) equipped with a stirrer and having an internal volume of 120 ml, then 20 ml of ethanol was added to the catalyst and thoroughly mixed under shaking. Thereafter, the resultant supernatant was removed from the autoclave by decantation. This operation was further repeated twice, and then the same operation was conducted three times except for using 20 ml of 1,2-dimethoxyethane in place of ethanol to effect the solvent replacement. The resultant supernatant which had finally been obtained was removed from the catalyst by decantation, and thereafter, 30 g of 1,2-dimethoxyethane and 5.00 g of glycidol were added thereto.

The reactor was tightly closed, and then the contents (atmosphere) of the autoclave were replaced with nitrogen, and further with hydrogen, sequentially, in the same manner as in Example 1, and a hydrogen pressure of 1.6 MPa (gauge pressure) was finally applied to the autoclave. Subsequently, while the contents of the autoclave were being stirred at 800 rpm, the temperature in the autoclave was elevated and the reaction was conducted at 100° C. for 5 hours. During the reaction, hydrogen was introduced into the autoclave so as to maintain the reaction pressure at a constant level.

When the reaction was completed, the reactor was cooled to room temperature and depressurized, and the contents of the autoclave were replaced with nitrogen, and then the reactor was opened. Thereafter, the supernatant was removed from the autoclave and the supernatant was analyzed by GC.

As a result of the calculation from the peak area ratios between the respective peaks appearing in the resultant GC chart, the conversion of glycidol was 75.7%, the selectivity for 1,3-propanediol was 50.9% and the selectivity for 1,2-propanediol was 8.2%. Further, according to the GC analysis, peaks corresponding to 3-hydroxypropionaldehyde, hydroxyacetone and propionaldehyde as carbonyl compounds were not detected.

Example 19

The catalyst carrying metal-Co on the silica carrier, which had been prepared in Example 12 was transferred to an autoclave made of stainless steel (mfd. by Taiatsu Glass K.K.) equipped with a stirrer and having an internal volume of 120 ml, then 20 ml of ethanol was added to the catalyst and thoroughly mixed under shaking. Thereafter, the resultant supernatant was removed from the autoclave by decantation. This operation was further repeated twice, and then the same operation was conducted three times except for using 20 ml of 1,2-dimethoxyethane in place of ethanol to effect the solvent replacement. The resultant supernatant which had finally been obtained was removed from the catalyst by decantation, and thereafter, 30 g of 1,2-dimethoxyethane and 5.00 g of glycidol were added thereto.

The reactor was tightly closed, and then the contents (atmosphere) of the autoclave were replaced with nitrogen, and further with hydrogen sequentially in the same manner as in Example 1, and a hydrogen pressure of 2.4 MPa (gauge pressure) was finally applied to the autoclave. Subsequently, while the contents of the autoclave were being stirred at 800 rpm, the temperature in the autoclave was elevated and the reaction was conducted at 80° C. for 5 hours. During the reaction, hydrogen was introduced into the autoclave so as to maintain the reaction pressure at a constant level.

When the reaction was completed, the reactor was cooled to room temperature and depressurized, and the contents of the autoclave were replaced with nitrogen, and then the reactor was opened. Thereafter, the supernatant was removed from the autoclave and the supernatant was analyzed by GC.

As a result of the calculation from the peak area ratios between the respective peaks appearing in the resultant GC chart, the conversion of glycidol was 35.3%, the selectivity for 1,3-propanediol was 65.8% and the selectivity for 1,2-propanediol was 9.4%. Further, according to the GC analysis, peaks corresponding to 3-hydroxypropionaldehyde, hydroxyacetone and propionaldehyde as carbonyl compounds were not detected.

Example 20

The catalyst carrying metal-Co on the silica carrier, which had been prepared in Example 12 was transferred to an autoclave made of stainless steel (mfd. by Taiatsu Glass K.K.) equipped with a stirrer and having an internal volume of 120 ml, then 20 ml of ethanol was added to the catalyst and thoroughly mixed under shaking. Thereafter, the resultant supernatant was removed from the autoclave by decantation. This operation was further repeated twice, and then the same operation was conducted three times except for using 20 ml of 1,2-dimethoxyethane in place of ethanol to effect the solvent replacement. The resultant supernatant which had finally been obtained was removed from the catalyst by decantation, and thereafter, 30 g of 1,2-dimethoxyethane and 5.00 g of glycidol were added thereto.

The reactor was tightly closed, and then the contents (atmosphere) of the autoclave were replaced with nitrogen, and further with hydrogen, sequentially, in the same manner as in Example 1, and a hydrogen pressure of 2.4 MPa (gauge pressure) was finally applied to the autoclave. Subsequently, while the contents of the autoclave were being stirred at 800 rpm, the temperature in the autoclave was elevated and the reaction was conducted at 60° C. for 5 hours. During the reaction, hydrogen was introduced into the autoclave so as to maintain the reaction pressure at a constant level.

When the reaction was completed, the reactor was cooled to room temperature and depressurized, and the contents of the autoclave were replaced with nitrogen, and then the reactor was opened. Thereafter, the supernatant was removed from the autoclave and the supernatant was analyzed by GC.

As a result of the calculation from the peak area ratios between the respective peaks appearing in the resultant GC chart, the conversion of glycidol was 19.3%, the selectivity for 1,3-propanediol was 78.4% and the selectivity for 1,2-propanediol was 7.6%. Further, according to the GC analysis, peaks corresponding to 3-hydroxypropionaldehyde, hydroxyacetone and propionaldehyde as carbonyl compounds were not detected.

Example 21

Preparation of Ru Catalyst Carried on Silica Carrier 6.630 g of an aqueous ruthenium nitrate solution containing 3.969 wt. % (mass %) of ruthenium was weighed in a beaker, and was used as Aqueous Solution (4). Then, 10.00 g of silica carrier (CARiACT Q-15) was added to the beaker containing therein Aqueous Solution (4), so as to cause the entire amount of Aqueous Solution (4) to be absorbed into the silica carrier.

The resultant silica carrier which had absorbed therein Aqueous Solution (4) was dried at 100° C. for one hour under a stream of nitrogen. Then, the silica carrier was reduced at 400° C. for two hours under a stream of hydrogen, to thereby prepare a catalyst carrying metal-Ru on the silica carrier.

Example 22

The catalyst carrying Ru on the silica carrier, which had been prepared in Example 21 was transferred to an autoclave made of stainless steel (mfd. by Taiatsu Glass K.K.) equipped with a stirrer and having an internal volume of 120 ml, then 20 ml of ethanol was added to the catalyst and thoroughly mixed under shaking. Thereafter, the resultant supernatant was removed from the autoclave by decantation. This operation was further repeated twice, and then the same operation was conducted three times except for using 20 ml of 1,2-dimethoxyethane in place of ethanol to effect the solvent replacement. The resultant supernatant which had finally been obtained was removed from the catalyst by decantation, and thereafter, 30 g of 1,2-dimethoxyethane and 5.00 g of glycidol were added thereto.

The reactor was tightly closed, and then the contents (atmosphere) of the autoclave were replaced with nitrogen, and further with hydrogen, sequentially, in the same manner as in Example 1, and a hydrogen pressure of 1.6 MPa (gauge pressure) was finally applied to the autoclave. Subsequently, while the contents of the autoclave were being stirred at 800 rpm, the temperature in the autoclave was elevated and the reaction was conducted at 80° C. for 5 hours. During the reaction, hydrogen was introduced into the autoclave so as to maintain the reaction pressure at a constant level.

When the reaction was completed, the reactor was cooled to room temperature and depressurized, and the contents of the autoclave were replaced with nitrogen, and then the reactor was opened. Thereafter, the supernatant was removed from the autoclave and the supernatant was analyzed by GC.

As a result of the calculation from the peak area ratios between the respective peaks appearing in the resultant GC chart, the conversion of glycidol was 16.1%, the selectivity for 1,3-propanediol was 57.3% and the selectivity for 1,2-propanediol was 19.7%. Further, according to the GC analysis, peaks corresponding to 3-hydroxypropionaldehyde, hydroxyacetone and propionaldehyde as carbonyl compounds were not detected.

Example 23

2.0 g of a sponge-Co catalyst (trade name: R-400, mfd. by Nikko Rika K.K.) wetted with water was transferred to an autoclave made of stainless steel (mfd. by Taiatsu Glass K.K.) equipped with a stirrer and having an internal volume of 120 ml, then 20 ml of ethanol was added to the catalyst and thoroughly mixed under shaking. Thereafter, the resultant supernatant was removed from the autoclave by decantation. This operation was further repeated twice, and then the same operation was conducted three times except for using 20 ml of 1,2-dimethoxyethane in place of ethanol to effect the solvent replacement. The resultant supernatant which had finally been obtained was removed from the catalyst by decantation, and thereafter, 30 g of 1,2-dimethoxyethane and 5.00 g of glycidol were added thereto.

The reactor was tightly closed, and then the contents (atmosphere) of the autoclave were replaced with nitrogen, and further with hydrogen, sequentially, in the same manner as in Example 1, and a hydrogen pressure of 1.6 MPa (gauge pressure) was finally applied to the autoclave. Subsequently, while the contents of the autoclave were being stirred at 800 rpm, the temperature in the autoclave was elevated and the reaction was conducted at 80° C. for 5 hours. During the reaction, hydrogen was introduced into the autoclave so as to maintain the reaction pressure at a constant level.

When the reaction was completed, the reactor was cooled to room temperature and depressurized, and the contents of the autoclave were replaced with nitrogen, and then the reactor was opened. Thereafter, the supernatant was removed from the autoclave and the supernatant was analyzed by GC.

As a result of the calculation from the peak area ratios between the respective peaks appearing in the resultant GC chart, the conversion of glycidol was 83.3%, the selectivity for 1,3-propanediol was 64.3% and the selectivity for 1,2-propanediol was 12.0%. Further, according to the GC analysis, peaks corresponding to 3-hydroxypropionaldehyde, hydroxyacetone and propionaldehyde as carbonyl compounds were not detected.

Example 24

2.0 g of a sponge-Co catalyst (trade name: R-400, mfd. by Nikko Rika K.K.) wetted with water was transferred to an autoclave made of stainless steel (mfd. by Taiatsu Glass K.K.) equipped with a stirrer and having an internal volume of 120 ml, then 20 ml of ethanol was added to the catalyst and thoroughly mixed under shaking. Thereafter, the resultant supernatant was removed from the autoclave by decantation. This operation was further repeated twice, and then the same operation was conducted three times except for using 20 ml of 1,2-dimethoxyethane in place of ethanol to effect the solvent replacement. The resultant supernatant which had finally been obtained was removed from the catalyst by decantation, and thereafter, 30 g of 1,2-dimethoxyethane and 5.00 g of glycidol were added thereto.

The reactor was tightly closed, and then the contents (atmosphere) of the autoclave were replaced with nitrogen, and further with hydrogen, sequentially, in the same manner as in Example 1, and a hydrogen pressure of 2.4 MPa (gauge pressure) was finally applied to the autoclave. Subsequently, while the contents of the autoclave were being stirred at 800 rpm, the temperature in the autoclave was elevated and the reaction was conducted at 60° C. for 5 hours. During the reaction, hydrogen was introduced into the autoclave so as to maintain the reaction pressure at a constant level.

When the reaction was completed, the reactor was cooled to room temperature and depressurized, and the contents of the autoclave were replaced with nitrogen, and then the reactor was opened. Thereafter, the supernatant was removed from the autoclave and the supernatant was analyzed by GC.

As a result of the calculation from the peak area ratios between the respective peaks appearing in the resultant GC chart, the conversion of glycidol was 83.1%, the selectivity for 1,3-propanediol was 65.1% and the selectivity for 1,2-propanediol was 12.5%. Further, according to the GC analysis, peaks corresponding to 3-hydroxypropionaldehyde, hydroxyacetone and propionaldehyde as carbonyl compounds were not detected.

Example 25

Preparation of Ni Catalyst Carried on Silica Carrier 2.752 g of nickel nitrate hexahydrate was weighed in a beaker, and 3.50 g of deionized water was added to the beaker to thereby prepare Aqueous Solution (5). Then, 5.00 g of silica carrier (CARiACT Q-15) was added to the beaker containing Aqueous Solution (5) which had been prepared therein, so as to cause the entire amount of Aqueous Solution (5) to be absorbed into the silica carrier.

The resultant silica carrier which had absorbed therein Aqueous Solution (5) was dried at 100° C. for one hour under a stream of nitrogen. Then, the silica carrier was reduced at 400° C. for two hours under a stream of hydrogen, to thereby prepare a catalyst carrying metal-nickel carried on the silica carrier.

Example 26

The catalyst carrying Ni carried on the silica carrier, which had been prepared in Example 25 was transferred to an autoclave made of stainless steel (mfd. by Taiatsu Glass K.K.) equipped with a stirrer and having an internal volume of 120 ml, then 20 ml of ethanol was added to the catalyst and thoroughly mixed under shaking. Thereafter, the resultant supernatant was removed from the autoclave by decantation. This operation was further repeated twice, and then the same operation was conducted three times except for using 20 ml of 1,2-dimethoxyethane in place of ethanol to effect the solvent replacement. The resultant supernatant which had finally been obtained was removed from the catalyst by decantation, and thereafter, 30 g of 1,2-dimethoxyethane and 5.00 g of glycidol were added thereto.

The reactor was tightly closed, and then the contents (atmosphere) of the autoclave were replaced with nitrogen, and further with hydrogen, sequentially, in the same manner as in Example 1, and a hydrogen pressure of 1.6 MPa (gauge pressure) was finally applied to the autoclave. Subsequently, while the contents of the autoclave were being stirred at 800 rpm, the temperature in the autoclave was elevated and the reaction was conducted at 100° C. for 5 hours. During the reaction, hydrogen was introduced into the autoclave so as to maintain the reaction pressure at a constant level.

When the reaction was completed, the reactor was cooled to room temperature and depressurized, and the contents of the autoclave were replaced with nitrogen, and then the reactor was opened. Thereafter, the supernatant was removed from the autoclave and the supernatant was analyzed by GC.

As a result of the calculation from the peak area ratios between the respective peaks appearing in the resultant GC chart, the conversion of glycidol was 74.9%, the selectivity for 1,3-propanediol was 41.9% and the selectivity for 1,2-propanediol was 53.3%. Further, according to the GC analysis, peaks corresponding to 3-hydroxypropionaldehyde, hydroxyacetone and propionaldehyde as carbonyl compounds were not detected.

Example 27

The catalyst carrying Ni carried on the silica carrier, which had been prepared in Example 25 was transferred to an autoclave made of stainless steel (mfd. by Taiatsu Glass K.K.) equipped with a stirrer and having an internal volume of 120 ml, then 20 ml of ethanol was added to the catalyst and thoroughly mixed under shaking. Thereafter, the resultant supernatant was removed from the autoclave by decantation. This operation was further repeated twice, and then the same operation was conducted three times except for using 20 ml of 1,2-dimethoxyethane in place of ethanol to effect the solvent replacement. The resultant supernatant which had finally been obtained was removed from the catalyst by decantation, and thereafter, 30 g of 1,2-dimethoxyethane and 5.00 g of glycidol were added thereto.

The reactor was tightly closed, and then the contents (atmosphere) of the autoclave were replaced with nitrogen, and further with hydrogen, sequentially, in the same manner as in Example 1, and a hydrogen pressure of 1.6 MPa (gauge pressure) was finally applied to the autoclave. Subsequently, while the contents of the autoclave were being stirred at 800 rpm, the temperature in the autoclave was elevated and the reaction was conducted at 120° C. for 5 hours. During the reaction, hydrogen was introduced into the autoclave so as to maintain the reaction pressure at a constant level.

When the reaction was completed, the reactor was cooled to room temperature and depressurized, and the contents of the autoclave were replaced with nitrogen, and then the reactor was opened. Thereafter, the supernatant was removed from the autoclave and the supernatant was analyzed by GC.

As a result of the calculation from the peak area ratios between the respective peaks appearing in the resultant GC chart, the conversion of glycidol was 96.9%, the selectivity for 1,3-propanediol was 57.5% and the selectivity for 1,2-propanediol was 35.4%. Further, according to the GC analysis, peaks corresponding to 3-hydroxypropionaldehyde, hydroxy acetone and propionaldehyde as carbonyl compounds were not detected.

Example 28

The catalyst carrying Ni carried on the silica carrier, which had been prepared in Example 25 was transferred to an autoclave made of stainless steel (mfd. by Taiatsu Glass K.K.) equipped with a stirrer and having an internal volume of 120 ml, then 20 ml of ethanol was added to the catalyst and thoroughly mixed under shaking. Thereafter, the resultant supernatant was removed from the autoclave by decantation. This operation was further repeated twice, and then the same operation was conducted three times except for using 20 ml of dioxane in place of ethanol to effect the solvent replacement. The resultant supernatant which had finally been obtained was removed from the catalyst by decantation, and thereafter, 30 g of dioxane and 5.00 g of glycidol were added thereto.

The reactor was tightly closed, and then the contents (atmosphere) of the autoclave were replaced with nitrogen, and further with hydrogen, sequentially, in the same manner as in Example 1, and a hydrogen pressure of 1.6 MPa (gauge pressure) was finally applied to the autoclave. Subsequently, while the contents of the autoclave were being stirred at 800 rpm, the temperature in the autoclave was elevated and the reaction was conducted at 120° C. for 5 hours. During the reaction, hydrogen was introduced into the autoclave so as to maintain the reaction pressure at a constant level.

When the reaction was completed, the reactor was cooled to room temperature and depressurized, and the contents of the autoclave were replaced with nitrogen, and then the reactor was opened. Thereafter, the supernatant was removed from the autoclave and the supernatant was analyzed by GC.

As a result of the calculation from the peak area ratios between the respective peaks appearing in the resultant GC chart, the conversion of glycidol was 98.8%, the selectivity for 1,3-propanediol was 61.5% and the selectivity for 1,2-propanediol was 29.6%, Further, according to the GC analysis, peaks corresponding to 3-hydroxypropionaldehyde, hydroxyacetone and propionaldehyde as carbonyl compounds were not detected.

Example 29

The catalyst carrying Ni carried on the silica carrier, which had been prepared in Example 25 was transferred to an autoclave made of stainless steel (mfd. by Taiatsu Glass K.K.) equipped with a stirrer and having an internal volume of 120 ml, then 20 ml of ethanol was added to the catalyst and thoroughly mixed under shaking. Thereafter, the resultant supernatant was removed from the autoclave by decantation. This operation was further repeated twice, and then the same operation was conducted three times except for using 20 ml of dioxane in place of ethanol to effect the solvent replacement. The resultant supernatant which had finally been obtained was removed from the catalyst by decantation, and thereafter, 30 g of dioxane and 5.00 g of glycidol were added thereto.

The reactor was tightly closed, and then the contents (atmosphere) of the autoclave were replaced with nitrogen, and further with hydrogen, sequentially, in the same manner as in Example 1, and a hydrogen pressure of 2.4 MPa (gauge pressure) was finally applied to the autoclave. Subsequently, while the contents of the autoclave were being stirred at 800 rpm, the temperature in the autoclave was elevated and the reaction was conducted at 120° C. for 5 hours. During the reaction, hydrogen was introduced into the autoclave so as to maintain the reaction pressure at a constant level.

When the reaction was completed, the reactor was cooled to room temperature and depressurized, and the contents of the autoclave were replaced with nitrogen, and then the reactor was opened. Thereafter, the supernatant was removed from the autoclave and the supernatant was analyzed by GC.

As a result of the calculation from the peak area ratios between the respective peaks appearing in the resultant GC chart, the conversion of glycidol was 99.0%, the selectivity for 1,3-propanediol was 57.5% and the selectivity for 1,2-propanediol was 35.5%. Further, according to the GC analysis, peaks corresponding to 3-hydroxypropionaldehyde, hydroxyacetone and propionaldehyde as carbonyl compounds were not detected.

Example 30

The catalyst carrying Ni carried on the silica carrier, which had been prepared in Example 25 was transferred to an autoclave made of stainless steel (mfd. by Taiatsu Glass K.K.) equipped with a stirrer and having an internal volume of 120 ml, then 20 ml of ethanol was added to the catalyst and thoroughly mixed under shaking. Thereafter, the resultant supernatant was removed from the autoclave by decantation. This operation was further repeated twice, and then the same operation was conducted three times except for using 20 ml of dioxane in place of ethanol to effect the solvent replacement. The resultant supernatant which had finally been obtained was removed from the catalyst by decantation, and thereafter, 30 g of dioxane and 5.00 g of glycidol were added thereto.

The reactor was tightly closed, and then the contents (atmosphere) of the autoclave were replaced with nitrogen, and further with hydrogen, sequentially, in the same manner as in Example 1, and a hydrogen pressure of 1.6 MPa (gauge pressure) was finally applied to the autoclave. Subsequently, while the contents of the autoclave were being stirred at 800 rpm, the temperature in the autoclave was elevated and the reaction was conducted at 140° C. for 5 hours. During the reaction, hydrogen was introduced into the autoclave so as to maintain the reaction pressure at a constant level.

When the reaction was completed, the reactor was cooled to room temperature and depressurized, and the contents of the autoclave were replaced with nitrogen, and then the reactor was opened. Thereafter, the supernatant was removed from the autoclave and the supernatant was analyzed by GC.

As a result of the calculation from the peak area ratios between the respective peaks appearing in the resultant GC chart, the conversion of glycidol was 100%, the selectivity for 1,3-propanediol was 64.2% and the selectivity for 1,2-propanediol was 20.0%. Further, according to the GC analysis, peaks corresponding to 3-hydroxypropionaldehyde, hydroxyacetone and propionaldehyde as carbonyl compounds were not detected.

Example 31

Preparation of Urushibara-Co Catalyst (U-Co-BA)

10 g of aluminum powder (40-80 mesh) was added into a 500 ml-beaker, and 50 ml of 1%-aqueous sodium hydroxide solution was added thereto, and the resultant mixture was stirred at room temperature (about 25° C.) for 10 minutes. Thereafter, the resultant supernatant was removed from the beaker, and further the residue was washed twice with 30 ml of hot water.

5 ml of water was added to the residue, and the resultant mixture was heated to 95° C., and thereafter was cooled to 40° C. Then, an aqueous solution of cobalt chloride hexahydrate (which had been obtained by dissolving 0.1 g of cobalt chloride hexahydrate in 18 ml of water) was added to the beaker, and the resultant mixture was subjected to a reaction by elevating the temperature thereof to 55° C. After the completion of the reaction, the reaction product was washed twice with 100 ml of hot water. 30 ml of water was added to the residue, and while the resultant mixture was cooled with ice, 250 ml of 20%-aqueous sodium hydroxide solution was added slowly to the mixture so that the temperature did not exceed 60° C. After the completion of the addition, the resultant mixture was heated to 50° C., and the stirring thereof was continued. When the production of hydrogen was terminated, the stirring was stopped, and the resultant supernatant was removed from the reaction mixture. Then, the residue was washed five times with 100 ml of hot water (until the supernatant showed neutrality), to thereby obtain a Co catalyst which had been suspended in water (amount: 2 g as metal Co).

Example 32

The Urushibara-Co catalyst (U-Co-BA), which had been prepared in Example 31 was transferred to an autoclave made of stainless steel (mfd. by Taiatsu Glass K.K.) equipped with a stirrer and having an internal volume of 120 ml, then 20 ml of ethanol was added to the catalyst and thoroughly mixed under shaking. Thereafter, the resultant supernatant was removed from the autoclave by decantation. This operation was further repeated twice, and then the same operation was conducted three times except for using 20 ml of 1,2-dimethoxyethane in place of ethanol to effect the solvent replacement. The resultant supernatant which had finally been obtained was removed from the catalyst by decantation, and thereafter, 30 g of 1,2-dimethoxyethane and 5.00 g of glycidol were added thereto.

The reactor was tightly closed, and then the contents (atmosphere) of the autoclave were replaced with nitrogen, and further with hydrogen, sequentially, in the same manner as in Example 1, and a hydrogen pressure of 1.6 Ma (gauge pressure) was finally applied to the autoclave. Subsequently, while the contents of the autoclave were being stirred at 800 rpm, the temperature in the autoclave was elevated and the reaction was conducted at 80° C. for 5 hours. During the reaction, hydrogen was introduced into the autoclave so as to maintain the reaction pressure at a constant level.

When the reaction was completed, the reactor was cooled to room temperature and depressurized, and the contents of the autoclave were replaced with nitrogen, and then the reactor was opened. Thereafter, the supernatant was removed from the autoclave and the supernatant was analyzed by GC.

As a result of the calculation from the peak area ratios between the respective peaks appearing in the resultant GC chart, the conversion of glycidol was 76.9%, the selectivity for 1,3-propanediol was 69.0% and the selectivity for 1,2-propanediol was 8.5%. Further, according to the GC analysis, peaks corresponding to 3-hydroxypropionaldehyde, hydroxyacetone and propionaldehyde as carbonyl compounds were not detected.

Example 33

The Urushibara-Co catalyst (U-Co-BA), which had been prepared in Example 31 was transferred to an autoclave made of stainless steel (mfd. by Taiatsu Glass K.K.) equipped with a stirrer and having an internal volume of 120 ml, then 20 ml of ethanol was added to the catalyst and thoroughly mixed under shaking. Thereafter, the resultant supernatant was removed from the autoclave by decantation. This operation was further repeated twice, and then the same operation was conducted three times except for using 20 ml of 1,2-dimethoxyethane in place of ethanol to effect the solvent replacement. The resultant supernatant which had finally been obtained was removed from the catalyst by decantation, and thereafter, 30 g of 1,2-dimethoxyethane and 5.00 g of glycidol were added thereto.

The reactor was tightly closed, and then the contents (atmosphere) of the autoclave were replaced with nitrogen, and further with hydrogen sequentially in the same manner as in Example 1, and a hydrogen pressure of 2.4 MPa (gauge pressure) was finally applied to the autoclave. Subsequently, while the contents of the autoclave were being stirred at 800 rpm, the temperature in the autoclave was elevated and the reaction was conducted at 80° C. for 5 hours. During the reaction, hydrogen was introduced into the autoclave so as to maintain the reaction pressure at a constant level.

When the reaction was completed, the reactor was cooled to room temperature and depressurized, and the contents of the autoclave were replaced with nitrogen, and then the reactor was opened. Thereafter, the supernatant was removed from the autoclave and the supernatant was analyzed by GC.

As a result of the calculation from the peak area ratios between the respective peaks appearing in the resultant GC chart, the conversion of glycidol was 99.8%, the selectivity for 1,3-propanediol was 67.6% and the selectivity for 1,2-propanediol was 7.8%. Further, according to the GC analysis, peaks corresponding to 3-hydroxypropionaldehyde, hydroxyacetone and propionaldehyde as carbonyl compounds were not detected.

INDUSTRIAL APPLICABILITY

As described hereinabove, a both end-hydroxyl group-terminated diol (e.g., propanediol) having an extremely low carbonyl impurity content can be produced with high efficiency, by using the catalyst for producing the both end-hydroxyl group-terminated diols, or the process for producing the both end-hydroxyl group-terminated diols by using the catalyst according to the present invention.

Further, the both end-hydroxyl group-terminated diols which can be obtained by the production process for such diols (particularly, 1,3-propanediol) according to the present invention have a high purity as compared with the 1,3-propanediols which had been obtained by conventional methods. When the thus obtained both end-hydroxyl group-terminated diols are used as a starting material for resins such as polyester, it is clear that a resin having little odor or coloring can be inexpensively produced.

What is claimed is:

1. A process for producing a both end-hydroxyl group-terminated diol, wherein an epoxy alcohol represented by the following general formula (1) is subjected to a hydrogenolysis reaction in the presence of a catalyst for producing both end-hydroxyl group terminated diols, which catalyst contains at least one element selected from the group consisting of Group V elements, Group VI elements, Group VII elements, Group VIII elements, Group IX elements, Group X elements, and Group XI elements in the periodic table, in the presence of at least one solvent selected from the group consisting of ethers, esters, aromatic hydrocarbon compounds, alicyclic hydrocarbon compounds and aliphatic hydrocarbon compounds, to thereby obtain a both end-hydroxyl group-terminated diol represented by the following general formula (2):

General formula (1):

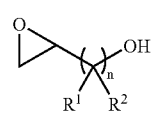

(1)

(wherein $R^1$ and $R^2$ each independently represents hydrogen, an alkyl group having 1 to 8 carbon atoms, a cycloalkyl group having 3 to 10 carbon atoms, or an aryl group having 6 to 13 carbon atoms and n represents an integer of 1 to 6);

General formula (2):

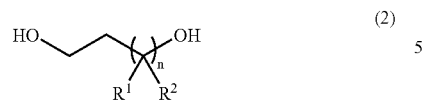
(2)

(wherein $R^1$ and $R^2$ each independently represents hydrogen, a cycloalkyl group, an aryl group or an alkyl group having 1 to 8 carbon atoms, and n represents an integer of 1 to 6).

2. A process for producing a both end-hydroxyl group-terminated diol according to claim 1, wherein the epoxy alcohol represented by general formula (1) is a compound which has been obtained by epoxidizing an unsaturated alcohol compound represented by general formula (3):

General Formula (3):

(3)

(wherein $R^1$ and $R^2$ each independently represents hydrogen, an alkyl group having 1 to 8 carbon atoms, a cycloalkyl group having 3 to 10 carbon atoms, or an aryl group having 6 to 13 carbon atoms and n represents an integer of 1 to 6).

3. A process for producing a both end-hydroxyl group-terminated diol represented by the general formula (2), which comprises at least the following Step (E) and Step (F):

Step (E): a step of epoxidizing an unsaturated alcohol compound represented by general formula (3), to thereby obtain an epoxy alcohol represented by the general formula (1);

Step (F): a step of subjecting the epoxy alcohol compound to a hydrogenolysis reaction in the presence of a catalyst for producing a both end-hydroxyl group-terminated diols, which catalyst contains at least one element selected from the group consisting of Group V elements, Group VI elements, Group VII elements, Group VIII elements, Group IX elements, Group X elements, and Group XI elements in the periodic table, and in the presence of at least one solvent selected from the group consisting of ethers, esters, aromatic hydrocarbon compounds, alicyclic hydrocarbon compounds and aliphatic hydrocarbon compounds, to thereby obtain a both end-hydroxyl group-terminated diol represented by the following general formula (2):

General formula (1)

(1)

(wherein $R^1$ and $R^2$ each independently represents hydrogen, an alkyl group having 1 to 8 carbon atoms, a cycloalkyl group having 3 to 10 carbon atoms, or an aryl group having 6 to 13 carbon atoms and n represents an integer of 1 to 6);

General formula (2):

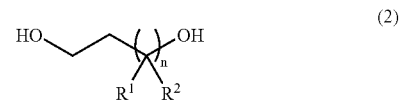
(2)

(wherein $R^1$ and $R^2$ each independently represents hydrogen, an alkyl group having 1 to 8 carbon atoms, a cycloalkyl group having 3 to 10 carbon atoms, or an aryl group having 6 to 13 carbon atoms and n represents an integer of 1 to 6)

General Formula (3):

(3)

(wherein $R^1$ and $R^2$ each independently represents hydrogen, an alkyl group having 1 to 8 carbon atoms, a cycloalkyl group having 3 to 10 carbon atoms, or an aryl group having 6 to 13 carbon atoms and n represents an integer of 1 to 6).

4. A process for producing a both end-hydroxyl group-terminated diol according to any of claims 1-3, wherein the epoxy alcohol represented by the following general formula (1) is at least one epoxy alcohol compound selected from the group consisting of: glycidol, 3,4-epoxy-1-butanol and 3,4-epoxy-2-butanol.

5. A process for producing a both end-hydroxyl group-terminated diol according to claims 2 or 3, wherein the unsaturated alcohol compound represented by general formula (3) is at least one unsaturated alcohol compound selected from the group consisting of: allyl alcohol, 3-buten-1-ol and 3-buten-2-ol.

6. A process for producing a both end-hydroxyl group-terminated diol according to any of claims 1 or 3, wherein the solvent is at least one species selected from the group consisting of diethyl ether, dibutyl ether, ethylene glycol dimethyl ether, ethylene glycol diethyl ether, 1,4-dioxane, benzene, toluene, xylene, cyclohexane, hexane, ethyl acetate, propyl acetate, isopropyl acetate and butyl acetate.

7. The process for producing both end-hydroxyl group-terminated diols according to any of claims 1, 2 or 3, wherein the catalyst comprises at least one element selected from the group consisting of Fe, Co, Ni, Cu, Re and Ru.

8. The process for producing both end-hydroxyl group-terminated diols according to claim 1 or 3, wherein the catalyst is a sponge catalyst.

9. The process for producing both end-hydroxyl group-terminated diols according to claim 1 or 3, wherein the catalyst is a carrier-containing catalyst.

10. The process for producing both end-hydroxyl group-terminated diols according to claim 9, wherein the carrier comprises at least one species selected form the group consisting of: activated carbon, alumina, silica, silica alumina, zeolite, diatomaceous earth, titania, and zirconia.

* * * * *